(12) United States Patent
Miller et al.

(10) Patent No.: US 7,897,823 B2
(45) Date of Patent: Mar. 1, 2011

(54) PROCESS FOR PRODUCTION OF AZEOTROPE COMPOSITIONS COMPRISING HYDROFLUOROOLEFIN AND HYDROGEN FLUORIDE AND USES OF SAID AZEOTROPE COMPOSITIONS IN SEPARATION PROCESSES

(75) Inventors: Ralpha Newton Miller, Newark, DE (US); Mario Joseph Nappa, Newark, DE (US); Velliyur Nott Mallikarjuna Rao, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 359 days.

(21) Appl. No.: 11/264,183

(22) Filed: Nov. 1, 2005

(65) Prior Publication Data

US 2006/0106263 A1    May 18, 2006

Related U.S. Application Data

(63) Continuation-in-part of application No. 11/259,901, filed on Oct. 27, 2005, now abandoned.

(60) Provisional application No. 60/623,210, filed on Oct. 29, 2004.

(51) Int. Cl.
*C07C 17/00*    (2006.01)
*C07C 17/25*    (2006.01)
*C07C 17/08*    (2006.01)
*C07C 17/18*    (2006.01)

(52) U.S. Cl. ........................ 570/155; 570/178
(58) Field of Classification Search ............. 570/155, 570/178
See application file for complete search history.

(56) References Cited

U.S. PATENT DOCUMENTS

| | | | |
|---|---|---|---|
| 2,480,560 A | 8/1949 | Downing et al. | |
| 2,599,631 A * | 6/1952 | Harmon ................. | 570/156 |
| 3,188,356 A | 6/1965 | Hauptschein et al. | |
| 4,766,260 A | 8/1988 | Manzer et al. | |
| 4,902,838 A | 2/1990 | Manzer et al. | |
| 4,978,649 A | 12/1990 | Surovikin et al. | |
| 5,136,113 A | 8/1992 | Rao | |
| 5,268,122 A | 12/1993 | Rao et al. | |
| 5,396,000 A * | 3/1995 | Nappa et al. ............ | 570/175 |
| 5,880,315 A * | 3/1999 | Rao et al. ............... | 570/157 |
| 5,918,481 A * | 7/1999 | Pham et al. ............. | 62/631 |
| 5,945,573 A * | 8/1999 | Nappa et al. ............ | 570/175 |
| 6,031,141 A * | 2/2000 | Mallikarjuna et al. .... | 570/136 |
| 6,093,859 A * | 7/2000 | Nappa et al. ............ | 570/175 |
| 6,369,284 B1 * | 4/2002 | Nappa et al. ............ | 570/156 |
| 6,388,147 B1 | 5/2002 | Rao et al. | |
| 6,476,281 B2 | 11/2002 | Qian et al. | |
| 6,540,882 B1 | 4/2003 | Reif et al. | |
| 6,540,933 B1 | 4/2003 | Sievert et al. | |
| 6,548,720 B2 | 4/2003 | Manogue et al. | |
| 6,703,533 B1 | 3/2004 | Belen'Kii et al. | |
| 7,388,117 B2 * | 6/2008 | Miller et al. ............ | 570/155 |
| 2002/0032356 A1 | 3/2002 | Gelblum et al. | |
| 2005/0177012 A1 | 8/2005 | Cohn et al. | |

FOREIGN PATENT DOCUMENTS

| | | | |
|---|---|---|---|
| EP | 0 234 002 A1 * | 9/1987 | |
| EP | 1 016 839 A2 | 7/2000 | |
| JP | 05 085970 A2 | 4/1993 | |
| JP | 1997067281 A | 3/1997 | |
| JP | 1997095459 A | 4/1997 | |
| WO | WO 97/29065 * | 8/1997 | |
| WO | WO 2004/018093 A2 | 3/2004 | |

OTHER PUBLICATIONS

International Search Report dated Aug. 31, 2006.

* cited by examiner

*Primary Examiner*—Daniel M Sullivan
*Assistant Examiner*—Chukwuma O Nwaonicha

(57) ABSTRACT

Disclosed herein is a process to produce an azeotrope composition comprising a hydrofluoroolefin and hydrogen fluoride, said process comprising, dehydrofluorinating a hydrofluorocarbon containing at least one hydrogen and at least one fluorine on adjacent carbons, thereby forming a mixture comprising said hydrofluoroolefin, unreacted hydrofluorocarbon and hydrogen fluoride, and distilling the mixture to produce a distillate composition comprising an azeotrope composition containing said hydrofluoroolefin and hydrogen fluoride and a column bottoms composition comprising said hydrofluorocarbon essentially free of hydrogen fluoride. Also disclosed herein are processes for separation of hydrofluoroolefins from hydrofluorocarbons and from hydrogen fluoride.

4 Claims, 1 Drawing Sheet

PROCESS FOR PRODUCTION OF AZEOTROPE COMPOSITIONS COMPRISING HYDROFLUOROOLEFIN AND HYDROGEN FLUORIDE AND USES OF SAID AZEOTROPE COMPOSITIONS IN SEPARATION PROCESSES

CROSS-REFERENCE TO RELATED APPLICATIONS

This application is a continuation-in-part of U.S. patent application Ser. No. 11/259,901 filed Oct. 27, 2005, now abandoned which claims the benefit of Provisional U.S. Patent Application No. 60/623,210 filed Oct. 29, 2004, both of which are incorporated herein by reference in their entireties.

BACKGROUND OF THE INVENTION

1. Field of the Invention

The present disclosure relates to the field of production and purification of hydrofluoroolefin compounds. The present disclosure further relates to processes utilizing azeotrope compositions for separation of hydrofluoroolefins from hydrofluorocarbons and hydrogen fluoride.

2. Description of Related Art

Chlorine-containing compounds such as chlorofluorocarbons (CFCs) are considered to be detrimental to the Earth's ozone layer. Many of the hydrofluorocarbons (HFCs), used to replace CFCs, have been found to contribute to global warming. Therefore, there is a need to identify new compounds that do not damage the environment, but also possess the properties necessary to function as refrigerants, solvents, cleaning agents, foam blowing agents, aerosol propellants, heat transfer media, dielectrics, fire extinguishing agents, sterilants and power cycle working fluids. Fluorinated olefins, especially those containing one or more hydrogens in the molecule (referred to herein as hydrofluoroolefins) are being considered for use in some of these applications such as in refrigeration as well as in processes to make fluoropolymers.

1,1,3,3,3-Pentafluoropropene is a useful cure-site monomer in polymerizations to form fluoroelastomers. U.S. Pat. Nos. 6,703,533, 6,548,720, 6,476,281, 6,369,284, 6,093,859, and 6,031,141, as well as published Japanese patent applications JP 09095459 and JP 09067281, and WIPO publication WO 2004018093, disclose processes wherein 1,1,1,3,3,3-hexafluoropropane is heated at temperatures below 500° C. in the presence of catalyst to form 1,1,3,3,3-pentafluoropropene. These low-temperature catalytic routes are chosen because of the well-known tendency for fluorocarbons to fragment at higher temperatures, e.g., above 500° C. This is made clear in Chemistry of Organic Fluorine Compounds, by Milos Hudlicky, $2^{nd}$ Revised Edition, Ellis Horwood PTR Prentice Hall [1992] p. 515: "Polyfluoroparaffins and especially fluorocarbons and other perfluoro derivates show remarkable heat stability. They usually do not decompose at temperatures below 300° C. Intentional decomposition, however, carried out at temperatures of 500-800° C., causes all possible splits in their molecules and produces complex mixtures which are difficult to separate."

U.S. Patent Application Publication 2002/0032356 discloses a process for producing the perfluorinated monomers tetrafluoroethylene and hexafluoropropylene in a gold-lined pyrolysis reactor.

The catalytic process has disadvantages, including catalyst preparation, start-up using fresh catalyst, catalyst deactivation, potential for plugging of catalyst-packed reactors with polymeric by-products, catalyst disposal or reactivation, and long reaction times that impose a space/time/yield reactor penalty. It would be desirable to be able to produce 1,1,3,3,3-pentafluoropropene from 1,1,1,3,3,3-hexafluoropropane in high yield by a non-catalytic process.

BRIEF SUMMARY OF THE INVENTION

One aspect relates to a process to produce a hydrofluoroolefin comprising dehydrofluorinating a hydrofluorocarbon containing at least one hydrogen and at least one fluorine on adjacent carbons, thereby forming a product mixture comprising said hydrofluoroolefin, unreacted hydrofluorocarbon and hydrogen fluoride, wherein at least one of said hydrofluoroolefin and said hydrofluorocarbon are present in said product mixture as an azeotrope composition with hydrogen fluoride.

A further aspect relates to a process for the separation of a hydrofluoroolefin from a hydrofluorocarbon wherein said hydrofluoroolefin contains one less fluorine atom and one less hydrogen atom than said hydrofluorocarbon, said process comprising: a) forming a mixture comprising hydrofluoroolefin, hydrofluorocarbon, and hydrogen fluoride; and b) subjecting said mixture to a distillation step forming a column distillate composition comprising an azeotrope or near-azeotrope composition of hydrogen fluoride and hydrofluoroolefin essentially free of said hydrofluorocarbon.

A further aspect relates to a process for the separation of a hydrofluoroolefin from a mixture comprising an azeotrope or near-azeotrope composition of said hydrofluoroolefin and hydrogen fluoride, said process comprising: a) subjecting said mixture to a first distillation step in which a composition enriched in either (i) hydrogen fluoride or (ii) hydrofluoroolefin is removed as a first distillate composition with a first bottoms composition being enriched in the other of said components (i) or (ii); and b) subjecting said first distillate composition to a second distillation step conducted at a different pressure in which the component enriched as first bottoms composition in (a) is removed as a second distillate composition with the second bottoms composition of the second distillation step enriched in the same component which was enriched in the first distillate composition.

A further aspect relates to a process for the purification of hydrofluoroolefin from a mixture of hydrofluoroolefin, hydrofluorocarbon, and hydrogen fluoride, said process comprising: a) subjecting said mixture to a first distillation step to form a first distillate composition comprising an azeotrope or near-azeotrope composition containing hydrofluoroolefin and hydrogen fluoride and a first bottoms composition comprising hydrofluorocarbon; b) subjecting said first distillate to a second distillation step from which a composition enriched in either (i) hydrogen fluoride or (ii) hydrofluoroolefin is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed as a third distillate composition with the third bottoms composition of the third distillation step enriched in the same component that was enriched in the second distillate composition.

A further aspect relates to a process to produce a hydrofluoroolefin comprising: a) feeding a hydrofluorocarbon containing at least one hydrogen and at least one fluorine on adjacent carbons to a reaction zone for dehydrofluorination to form a reaction product composition comprising hydrofluoroolefin, unreacted hydrofluorocarbon and hydrogen fluoride; b) subjecting said reaction product composition to a first distillation step to form a first distillate composition comprising an azeotrope or near-azeotrope composition containing hydrofluoroolefin and hydrogen fluoride and a first bottoms composition comprising hydrofluorocarbon; c) subjecting said first distillate composition to a second distillation step from which a composition enriched in either (i) hydrogen fluoride or (ii) hydrofluoroolefin is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (c) is removed as a third distillate composition with the third bottoms composition of the third distillation step enriched in the same component that was enriched in the second distillate composition.

A further aspect is for a hydrofluoroolefin selected from the group consisting of $CF_2=C(CHF_2)_2$, $CHF=C(CHF_2)_2$, $CH_2=C(CH_2F)CF_3$, $CH_2=CFCF_2CF_2CF_3$, $CHF_2CF_2CF=CFCH_3$, $CF_3CF_2CF=CHCH_3$, $(CF_3)_2C=CFCHF_2$, $(CF_3)_2CFCF=CHCH_3$, $(CF_3)_2C=C(CH_3)_2$, $(CH_3)_2C=CFCF_2CF_3$, $C_2F_5CH=CHCF_2C_2F_5$, $CF_3CH=CHCF_2C_2F_5$, $CF_3CF_2CF_2CF_2CF=CHCH_3$, $CF_3CF_2CF_2CF=CHCH_2CH_3$, $(CH_3)_2C=CFCF_2CF_2CF_3$, and $CF_3CH=CFCH_2CF_3$.

Another aspect provides a process for producing $CF_3CH=CF_2$ in the absence of dehydrofluorination catalyst. In particular, this aspect comprises pyrolyzing $CF_3CH_2CF_3$ to make $CF_3CH=CF_2$. Pyrolyzing accomplishes the thermal decomposition of the $CF_3CH_2CF_3$, at a temperature greater than about 700° C.

This selective formation of $CF_3CH=CF_2$ embodies several unexpected results. First, it is surprising that the heat input of the pyrolysis process does not cause the $CF_3CH_2CF_3$ reactant to fragment to C-1, e.g., methanes, and C-2, e.g., ethane and ethylene, compounds. Second, it is surprising that the $CF_3CH=CF_2$ product is stable under pyrolysis conditions and does not undergo further conversion to rearranged products or to products containing fewer hydrogen and/or fluorine atoms. Third, it is surprising that the pyrolysis to form $CF_3CH=CF_2$ takes place with high selectivity.

BRIEF DESCRIPTION OF THE DRAWING(S)

DETAILED DESCRIPTION OF THE INVENTION

Figure 2:
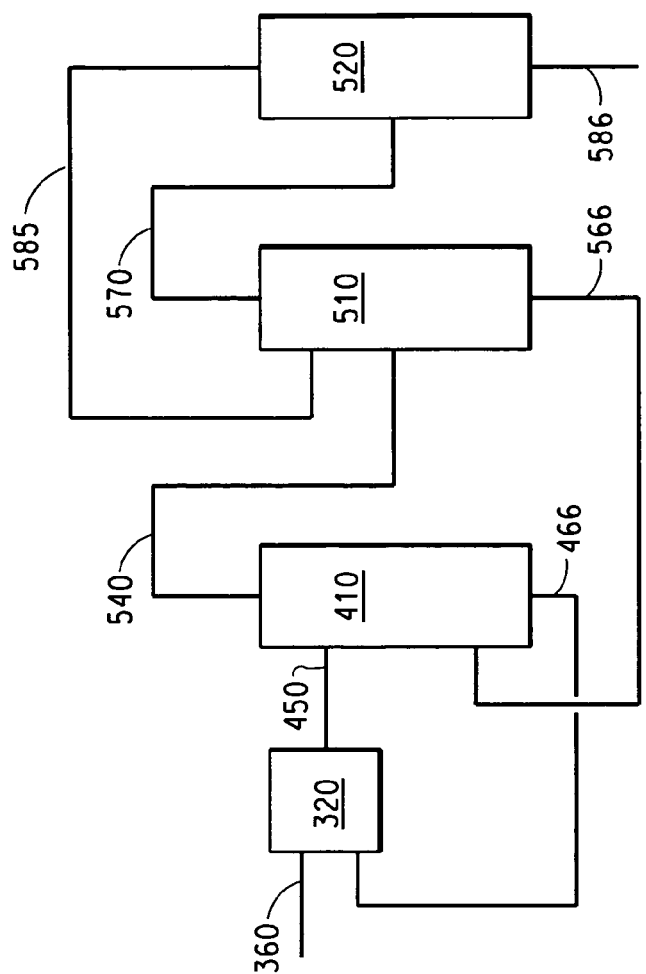
FIG. 2 is a schematic flow diagram illustrating one embodiment for practicing a process for production of hydrofluoroolefin.

One aspect relates to processes to produce and processes to purify hydrofluoroolefins. The processes to purify include processes to separate hydrofluoroolefins from hydrogen fluoride and processes to separate hydrofluoroolefins from hydrofluorocarbons and hydrogen fluoride, said processes utilizing azeotrope or near-azeotrope compositions.

A further aspect provides a process to produce a hydrofluoroolefin comprising dehydrofluorinating a hydrofluorocarbon containing at least one hydrogen and at least one fluorine on adjacent carbons, thereby forming a product mixture comprising said hydrofluoroolefin, unreacted hydrofluorocarbon and hydrogen fluoride, wherein at least one of said hydrofluoroolefin and said hydrofluorocarbon are present in said product mixture as an azeotrope composition with hydrogen fluoride.

The hydrofluoroolefins are acyclic compounds containing 3 to 8 carbon atoms, fluorine and hydrogen. Hydrofluoroolefins must also contain at least one double bond and may be linear or branched. The acyclic hydrofluoroolefins may be represented by the formula, $C_xH_{a-1}F_{b-1}$, wherein x is an integer from 3 to 8, a is an integer from 2 to (x+1), b is an integer from (x+1) to (2x) and wherein a+b=2x+2. Representative hydrofluoroolefins include, but are not limited to, trifluoropropenes, tetrafluoropropenes, pentafluoropropenes, tetrafluorobutenes, pentafluorobutenes, hexafluorobutenes, heptafluorobutenes, pentafluoropentenes, hexafluoropentenes, heptafluoropentenes, octafluoropentenes, nonafluoropentenes, hexafluorohexenes, heptafluorohexenes, octafluorohexenes, nonafluorohexenes, decafluorohexenes, undecafluorohexenes, heptafluoroheptenes, octafluoroheptenes, nonafluoroheptenes, decafluoroheptenes, undecafluoroheptenes, dodecafluoroheptenes, tridecafluoroheptenes, octafluorooctenes, nonafluorooctenes, decafluorooctenes, undecafluorooctenes, dodecafluorooctenes, tridecafluorooctenes, tetradecafluorooctenes, and pentadecafluorooctenes.

Also included are cyclic hydrofluoroolefins containing a total of 4 to 8 carbon atoms including 4 to 6 carbon atoms in the ring. Cyclic hydrofluoroolefins must also contain at least one double bond and may have branching on the ring. The cyclic hydrofluoroolefins may be represented by the formula, $C_yH_{c-1}F_{d-1}$, wherein y is an integer from 4 to 8, c is an integer from 2 to y, d in an integer from y to (2y−2) and wherein c+d=2y. Representative cyclic hydrofluoroolefins include, but are not limited to, difluorocyclopropenes, trifluorocyclopropenes, trifluorocyclobutenes, tetrafluorocyclobutenes, pentafluorocyclobutenes, trifluoromethylcyclopropenes, tetrafluoromethylcyclopropenes, pentafluoromethylcyclopropenes, tetrafluorocyclopentenes, pentafluorocyclopentenes, hexafluorocyclopentenes, heptafluorocyclopentenes, tetrafluorodimethylcyclopropenes, pentafluorodimethylcyclopropenes, hexafluorodimethylcyclopropenes, heptafluorodimethylcyclopropenes, tetrafluoroethylcyclopropenes, pentafluoroethylcyclopropenes, hexafluoroethylcyclopropenes, heptafluoroethylcyclopropenes, tetrafluoromethylcyclobutenes, pentafluoromethylcyclobutenes, hexafluoromethylcyclobutenes, heptafluoromethylcyclobutenes, pentafluorocyclohexenes, hexafluorocyclohexenes, heptafluorocyclohexenes, octafluorocyclohexenes, nonafluorocyclohexenes, pentafluoromethylcyclopentenes, hexafluoromethylcyclopentenes, heptafluoromethylcyclopentenes, octafluoromethylcyclopentenes, nonafluoromethylcyclopentenes, pentafluorodimethylcyclobutenes, hexafluorodimethylcyclobutenes, heptafluorodimethylcyclobutenes, octafluorodimethylcyclobutenes, nonafluorodimethylcyclobutenes, pentafluoroethylcyclobutenes, hexafluoroethylcyclobutenes, heptafluoroethylcyclobutenes, octafluoroethylcyclobutenes, nonafluoroethylcyclobutenes, pentafluorotrimethylcyclopropenes, hexafluorotrimethylcyclopropenes, heptafluorotrimethylcyclopropenes, octafluorotrimethylcyclopropenes, and nonafluorotrimethylcyclopropenes.

The hydrofluoroolefins may exist as different configurational isomers or stereoisomers. Included are all single configurational isomers, single stereoisomers or any combination thereof. For instance, HFC-1234 ze ($CF_3CH=CHF$) is meant to represent the E-isomer, Z-isomer, or any combination or mixture of both isomers in any ratio. Another example is HFC-1336mzz ($CF_3CH=CHCF_3$), by which is represented the E-isomer, Z-isomer, or any combination or mixture of both isomers in any ratio.

The hydrofluorocarbons are acyclic, linear or branched compounds containing 3 to 8 carbon atoms, hydrogen and fluorine. At least one hydrogen atom and at least one fluorine atom must be on adjacent carbon atoms. The hydrofluorocarbons may be represented by the formula $C_xH_aF_b$, wherein x is an integer from 3 to 8, a is an integer from 2 to (x+1), b is an integer from (x+1) to (2x) and wherein a+b=2x+2. The hydrofluorocarbons are precursor compounds for the hydrofluoroolefins. The hydrofluorocarbons may be dehydrofluorinated in the vapor phase to form the hydrofluoroolefins of the present invention along with hydrogen fluoride co-product.

Also included are cyclic hydrofluorocarbons containing a total of 4 to 8 carbon atoms and with the ring comprising 4 to 6 carbon atoms. At least one hydrogen atom and at least one fluorine atom must be on adjacent carbon atoms. The cyclic hydrofluorocarbons may be represented by the formula $C_yH_cF_d$, wherein y is an integer from 4 to 8, c is an integer from 2 to y, d is an integer from y to (2y−2) and wherein c+d=2y. The cyclic hydrofluorocarbons are precursor compounds for the cyclic hydrofluoroolefins. The cyclic hydrofluorocarbons may be dehydrofluorinated in the vapor phase to form the cyclic hydrofluoroolefins of the present invention along with hydrogen fluoride co-product.

The list in Table 1 indicates representative hydrofluoroolefins and the corresponding precursor hydrofluorocarbons. The list in Table 2 indicates representative cyclic hydrofluoroolefins and the corresponding precursor cyclic hydrofluorocarbons. Depending on the number and position of hydrogen and fluorine atoms in a particular precursor hydrofluorocarbon, and provided that at least one hydrogen atom and at least one fluorine atom must be on adjacent carbon atoms, more than one hydrofluoroolefin may be produced. Tables 1 and 2 indicate one representative hydrofluoroolefin from a precursor hydrofluorocarbon and in some instances more than one hydrofluoroolefin from a precursor hydrofluorocarbon.

TABLE 1

| Hydrofluorocarbon | Hydrofluoroolefin(s) |
|---|---|
| $CF_3CF_2CH_2F$ | $CF_3CF=CHF$ |
| $CF_3CHFCHF_2$ | $CF_3CF=CHF$ |
| $CF_3CH_2CF_3$ | $CF_3CH=CF_2$ |
| $CHF_2CF_2CH_2F$ | $CHF_2CF=CHF$ |
| $CHF_2CHFCHF_2$ | $CHF_2CF=CHF$ |
| $CF_3CF_2CH_3$ | $CF_3CF=CH_2$ |
| $CF_3CHFCH_2F$ | $CF_3CF=CH_2$ |
| $CF_3CH_2CHF_2$ | $CF_3CH=CHF$ |
| $CH_2FCF_2CH_2F$ | $CH_2FCF=CHF$ |
| $CH_3CF_2CHF_2$ | $CHF_2CF=CH_2$ |
| $CHF_2CHFCH_2F$ | $CHF_2CF=CH_2$ |
| $CF_3CH_2CH_2F$ | $CF_3CH=CH_2$ |
| $CF_3CHFCH_3$ | $CF_3CH=CH_2$ |
| $CHF_2CH_2CHF_2$ | $CHF_2CH=CHF$ |
| $CH_2FCF_2CF_2CF_3$ | $CHF=CFCF_2CF_3$ |
| $CF_3CHFCF_2CHF_2$ | $CF_3CF=CFCHF_2$ |
| $CF_3CH_2CF_2CF_3$ | $CF_3CH=CFCF_3$ |
| $CF_3CHFCHFCF_3$ | $CF_3CH=CFCF_3$ |
| $CH_3CF_2CF_2CF_3$ | $CH_2=CFCF_2CF_3$ |
| $CH_2FCHFCF_2CF_3$ | $CH_2=CFCF_2CF_3$ |
| $CF_3CHFCF_2CH_2F$ | $CF_3CF=CFCH_2F$ |
| $CH_2FCF_2CF_2CHF_2$ | $CHF=CFCF_2CHF_2$ |
| $CHF_2CH_2CF_2CF_3$ | $CHF_2CH=CFCF_3$ |
| $CHF_2CHFCHFCF_3$ | $CHF_2CF=CHCF_3$ and/or $CHF_2CH=CFCF_3$ |
| $CHF_2CHFCF_2CHF_2$ | $CHF_2CF=CFCHF_2$ |
| $CHF_2CF_2CH_2CF_3$ | $CHF_2CF=CHCF_3$ |
| $CF_3CH_2CHFCF_3$ | $CF_3CH=CHCF_3$ |

TABLE 1-continued

| Hydrofluorocarbon | Hydrofluoroolefin(s) |
|---|---|
| $CF_3CHFCF_2CH_3$ | $CF_3CF=CFCH_3$ |
| $CF_3CF_2CHFCH_3$ | $CF_3CF=CFCH_3$ |
| $CH_3CF_2CF_2CHF_2$ | $CH_2=CFCF_2CHF_2$ |
| $CF_3CH_2CF_2CH_2F$ | $CF_3CH=CFCH_2F$ |
| $CF_3CF_2CH_2CH_2F$ | $CF_3CF=CHCH_2F$ and/or $CF_3CH=CH_2$ |
| $CH_2FCHFCHFCF_3$ | $CH_2FCF=CHCF_3$ and/or $CH_2FCH=CFCF_3$ |
| $CHF_2CF_2CHFCH_2F$ | $CHF_2CF=CFCH_2F$ and/or $CHF_2CF=CH_2$ |
| $CF_3CH_2CH_2CF_3$ | $CF_3CH_2CH=CF_2$ |
| $CHF_2CH_2CHCF_3$ | $CHF_2CH=CHCF_3$ |
| $CHF_2CHFCH_2CF_3$ | $CHF_2CH=CHCF_3$ |
| $CHF_2CH_2CF_2CHF_2$ | $CHF_2CH=CFCHF_2$ |
| $CHF_2CHFCHFCHF_2$ | $CHF_2CH=CFCHF_2$ |
| $CF_3CF_2CH_2CH_3$ | $CF_3CF=CHCH_3$ |
| $CF_3CH_2CF_2CH_3$ | $CF_3CH=CFCH_3$ |
| $CH_3CHFCF_2CF_3$ | $CH_3CF=CHCF_3$ and/or $CH_3CH=CFCF_3$ |
| $CH_3CHFCF_2CHF_2$ | $CH_3CF=CFCHF_2$ |
| $CH_2FCH_2CHFCF_3$ | $CH_2FCH=CHCF_3$ |
| $CH_2FCHFCH_2CF_3$ | $CH_2FCH=CHCF_3$ |
| $CH_2FCH_2CF_2CHF_2$ | $CH_2FCH=CFCHF_2$ |
| $CH_2FCHFCHFCHF_2$ | $CH_2FCF=CHCHF_2$ and/or $CH_2FCH=CFCHF_2$ |
| $CHF_2CH_2CH_2CF_3$ | $CHF=CHCH_2CF_3$ |
| $CHF_2CH(CF_3)_2$ | $CHF=C(CF_3)_2$ |
| $CH_2FCF(CF_3)_2$ | $CHF=C(CF_3)_2$ |
| $CH_3CF(CF_3)_2$ | $CH_2=C(CF_3)_2$ |
| $CH_2FCH(CF_3)_2$ | $CH_2=C(CF_3)_2$ |
| $CHF_2CF(CHF_2)_2$ | $CF_2=C(CHF_2)_2$ |
| $CH_3CHHHHH(CF_3)_2$ | $CF_2=C(CF_3)CH_3$ |
| $CF_3CHHHHH(CH_2F)_2$ | $CH_2=C(CF_3)CH_2F$ |
| $CHF_2CH(CHF_2)_2$ | $CHF=C(CHF_2)_2$ |
| $CH_3CF(CHF_2)_2$ | $CH_2=C(CHF_2)_2$ |
| $CH_2FCH(CH_2F)CF_3$ | $CH_2=C(CH_2F)CF_3$ |
| $CH_2FCH(CHF_2)_2$ | $CH_2=C(CHF_2)_2$ |
| $CF_3CHFCHFCF_2CF_3$ | $CF_3CH=CFCF_2CF_3$ and/or $CF_3CF=CHCF_2CF_3$ |
| $CF_3CF_2CH_2CF_2CF_3$ | $CF_3CF_2CH=CFCF_3$ |
| $CF_3CH_2CF_2CF_2CF_3$ | $CF_3CH=CFCF_2CF_3$ |
| $CF_3CH_2CHFCF_2CF_3$ | $CF_3CH=CHCF_2CF_3$ |
| $CF_3CHFCH_2CF_2CF_3$ | $CF_3CH=CHCF_2CF_3$ |
| $CF_3CF_2CF_2CF_2CF_3$ | $CH_2=CFCF_2CF_2CF_3$ |
| $CH_3CF_2CF_2CF_2CHF_2$ | $CH_2=CFCF_2CF_2CHF_2$ |
| $CF_3CH_2CF_2CH_2CF_3$ | $CF_3CH=CFCH_2CF_3$ |
| $CHF_2CF_2CF_2CHFCH_3$ | $CHF_2CF_2CF=CFCH_3$ |
| $CF_3CF_2CF_2CH_2CH_3$ | $CF_3CF_2CF=CHCH_3$ |
| $(CF_3)_2CFCH_2CF_3$ | $(CF_3)_2C=CHCF_3$ |
| $(CF_3)_2CHCHFCF_3$ | $(CF_3)_2C=CHCF_3$ |
| $(CF_3)_2CFCHFCHF_2$ | $(CF_3)_2C=CFCHF_2$ |
| $(CF_3)_2CFCH_2CHF_2$ | $(CF_3)_2C=CHCHF_2$ |
| $(CF_3)_2CFCH_2CH_3$ | $(CF_3)_2C=CHCH_3$ |
| $CF_3CF_2CHFCHFCF_2CF_3$ | $CF_3CF_2CH=CFCF_2CF_3$ |
| $CH_2FCHFCF_2CF_2CF_2CF_3$ | $CH_2=CFCF_2CF_2CF_2CF_3$ |
| $CF_3CH_2CHFCF_2CF_2CF_3$ | $CF_3CH=CHCF_2CF_2CF_3$ |
| $CF_3CHFCH_2CF_2CF_2CF_3$ | $CF_3CH=CHCF_2CF_2CF_3$ |
| $CF_3CF_2CH_2CHFCF_2CF_3$ | $CF_3CF_2CH=CHCF_2CF_3$ |
| $CF_3CH_2CF_2CF_2CH_2CF_3$ | $CF_3CH=CFCF_2CH_2CF_3$ |
| $CF_3CF_2CH_2CH_2CF_2CF_3$ | $CF_3CF=CHCH_2CF_2CF_3$ |
| $CH_3CH_2CF_2CF_2CF_2CF_3$ | $CH_3CH=CFCF_2CF_2CF_3$ |
| $CH_3CHFCF_2CF_2CF_2CF_3$ | $CH_2=CHCF_2CF_2CF_2CF_3$ |
| $CF_3CF_2CF_2CH_2CHFCH_3$ | $CF_3CF_2CF_2CH=CHCH_3$ |
| $(CF_3)_2CFCF_2CH_2CH_3$ | $(CF_3)_2CFCF=CHCH_3$ |
| $(CF_3)_2CFCH_2CH_2CH_3$ | $(CF_3)_2C=CHCH_2CH_3$ |
| $(CF_3)_2CHCH_2CF_2CF_3$ | $(CF_3)_2C=CHCF_2CF_3$ |
| $(CF_3)_2CFCHFCHFCF_3$ | $(CF_3)_2C=CFCHFCF_3$ and/or $(CF_3)_2CFCF=CHCF_3$ and/or $(CF_3)_2CFCH=CFCF_3$ |
| $(CF_3)_2CHCH_2CF_2CF_3$ | $(CF_3)_2CHCH=CFCF_3$ |
| $(CF_3)_2CFCH(CH_3)_2$ | $(CF_3)_2C=C(CH_3)_2$ |
| $(CH_3)_2CHCF_2CF_2CF_3$ | $(CH_3)_2C=CFCF_2CF_3$ |
| $C_2F_5CHFCHFCF_2C_2F_5$ | $C_2F_5CF=CHCF_2C_2F_5$ and/or $C_2F_5CH=CFCF_2C_2F_5$ |
| $CF_3CHFCHFCF_2CF_2C_2F_5$ | $CF_3CF=CHCF_2CF_2C_2F_5$ and/or $CF_3CH=CFCF_2CF_2C_2F_5$ |
| $C_2F_5CHFCH_2CF_2C_2F_5$ | $C_2F_5CH=CHCF_2C_2F$ |
| $C_2F_5CH_2CHFCF_2C_2F_5$ | $C_2F_5CH=CHCF_2C_2F_5$ |

TABLE 1-continued

| Hydrofluorocarbon | Hydrofluoroolefin(s) |
|---|---|
| $CF_3CHFCH_2CF_2CF_2C_2F_5$ | $CF_3CH=CHCF_2CF_2C_2F_5$ |
| $CF_3CH_2CHFCF_2CF_2C_2F_5$ | $CF_3CH=CHCF_2CF_2C_2F_5$ |
| $CHF_2CF_2CF_2CF_2CF_2CF_2CH_3$ | $CHF_2CF_2CF_2CF_2CF_2CF=CH_2$ |
| $CF_3CF_2CF_2CF_2CF_2CH_2CH_3$ | $CF_3CF_2CF_2CF_2CF=CHCH_3$ |
| $CF_3CF_2CF_2CF_2CH_2CH_2CH_3$ | $CF_3CF_2CF_2CF=CHCH_2CH_3$ |
| $CF_3CF_2C(CH_3)HCH_2CF_2CF_3$ | $CF_3CF_2CH(CH_3)CH=CFCF_3$ |
| $(CH_3)_2CHCF_2CF_2CF_2CF_3$ | $(CH_3)_2C=CFCF_2CF_2CF_3$ |
| $C_2F_5CHFCHFCF_2CF_2C_2F_5$ | $C_2F_5CF=CHCF_2CF_2C_2F_5$ and/or $C_2F_5CH=CFCF_2CF_2C_2F_5$ |
| $C_2F_5CF_2CHFCHFCF_2C_2F_5$ | $C_2F_5CF_2CF=CHCF_2C_2F_5$ |
| $CF_3(CF_2)_5CH_2CH_2F$ | $CF_3(CF_2)_5CH=CH_2$ |
| $CF_3(CF_2)_5CH_2CH_3$ | $CF_3(CF_2)_4CF=CHCH_3$ |
| $CF_3(CF_2)_3CH_2CH_2CHFCH_3$ | $CF_3(CF_2)_3CH_2CH_2CH=CH_2$ and/or $CF_3(CF_2)_3CH_2CH=CHCH_3$ |

TABLE 2

| Hydrofluorocarbon | Hydrofluoroolefin |
|---|---|
| cyclo-$CF_2CF_2CF_2CH_2$— | cyclo-$CF_2CF_2CF=CH$— |
| cyclo-$CF_2CF_2CHFCHF$— | cyclo-$CF_2CF_2CF=CH$— |
| cyclo-$CF_2CF_2CH_2CH_2$— | cyclo-$CF_2CH_2CH=CF$— |
| cyclo-$CF_2CF_2CF_2CHFCHF$— | cyclo-$CF_2CF_2CF_2CF=CH$— |
| cyclo-$CF_2CF_2CF_2CF_2CHFCHF$— | cyclo-$CF_2CF_2CF_2CF_2CF=CH$— |
| cyclo-$CF_2CF_2CHFCF_2CF_2CHF$— | cyclo-$CF_2CF_2CHFCF_2CF=CF$— |

The hydrofluorocarbons are available commercially, may be made by methods known in the art, or may be made as described herein.

1,1,1,2,3,3-Hexafluoro-2-(trifluoromethyl)-pentane (($CF_3)_2CFCF_2CH_2CH_3$) may be prepared by the reaction of 1,1,1,2,3,3-hexafluoro-2-(trifluoromethyl)-3-iodo-propane with ethylene to give 1,1,1,2,3,3-hexafluoro-2-(trifluoromethyl)-5-iodopentane followed by zinc reduction in an acid such as HCl or acetic acid.

1,1,1,2-Tetrafluoro-2-(trifluoromethyl)-pentane (($CF_3)_2CFCH_2CH_2CH_3$) may be prepared by reacting methyl perfluoroisobutyrate with ethyl magnesium bromide followed by hydrolysis to give 1,1,1,2-tetrafluoro-2-(trifluoromethyl)-3-pentanol. The pentanol is converted to 4,5,5,5-tetrafluoro-4-(trifluoromethyl)-2-pentene by dehydration with phosphorous pentoxide and the double bond saturated by hydrogenation over a palladium on carbon catalyst.

1,1,1,2,2,3,3,4,4,5,5-Undecafluoroheptane ($CF_3CF_2CF_2CF_2CF_2CH_2CH_3$) may be prepared by reaction of 1,1,1,2,2,3,3,4,4,5,5-undecafluoro-5-iodo-pentane with ethylene to give 1,1,1,2,2,3,3,4,4,5,5-undecafluoro-7-iodoheptane followed by zinc reduction in an acid such as HCl or acetic acid.

As mentioned earlier, certain precursor hydrofluorocarbons listed in Tables 1 and also in Table 2 may produce a single hydrofluoroolefin or a mixture of 2 or more hydrofluoroolefins as a result of the dehydrofluorination reaction. Included are the pairs of the hydrofluorocarbon and each hydrofluoroolefin individually or the hydrofluorocarbon and the mixtures of 2 or more hydrofluoroolefin compounds that may be produced by any specific reaction.

Anhydrous hydrogen fluoride (HF) is also useful in the processes and is commercially available.

One aspect relates to a process to produce a hydrofluoroolefin comprising dehydrofluorinating a hydrofluorocarbon containing at least one hydrogen and at least one fluorine on adjacent carbons, thereby forming a product mixture comprising said hydrofluoroolefin, unreacted hydrofluorocarbon and hydrogen fluoride, wherein at least one of said hydrofluoroolefin and said hydrofluorocarbon are present in said product mixture as an azeotrope composition with hydrogen fluoride.

The dehydrofluorination of a hydrofluorocarbon may be carried out in the vapor phase. Vapor phase dehydrofluorination of a hydrofluorocarbon may be suitably carried out using typical dehydrofluorination catalysts. Generally, the present dehydrofluorination may be carried out using any dehydrofluorination catalyst known in the art. These catalysts include, but are not limited to, aluminum fluoride; fluorided alumina; metals on aluminum fluoride; metals on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, and cubic chromium trifluoride; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof.

Dehydrofluorination catalysts include aluminum fluoride, fluorided alumina, metals on aluminum fluoride, and metals on fluorided alumina, as disclosed in U.S. Pat. No. 5,396,000, incorporated herein by reference. Fluorided alumina and aluminum fluoride can be prepared as described in U.S. Pat. No. 4,902,838, incorporated herein by reference. Suitable metals include chromium, magnesium (e.g., magnesium fluoride), Group VIIB metals (e.g., manganese), Group IIIB metals (e.g., lanthanum), and zinc. In use, such metals are normally present as halides (e.g., fluorides), as oxides and/or as oxyhalides. Metals on aluminum fluoride and metals on fluorided alumina can be prepared by procedures as described in U.S. Pat. No. 4,766,260, incorporated herein by reference. In one embodiment, when supported metals are used, the total metal content of the catalyst is from about 0.1 to 20 percent by weight, typically from about 0.1 to 10 percent by weight. Preferred catalysts include catalysts consisting essentially of aluminum fluoride and/or fluorided alumina.

Additionally, dehydrofluorination catalysts include oxides, fluorides, and oxyfluorides of magnesium, zinc and mixtures of magnesium and zinc and/or aluminum. A suitable catalyst may be prepared, for example by drying magnesium oxide until essentially all water is removed, e.g., for about 18 hours at about 100° C. The dried material is then transferred to the reactor to be used. The temperature is then gradually increased to about 400° C. while maintaining a flow of nitrogen through the reactor to remove any remaining traces of moisture from the magnesium oxide and the reactor. The temperature is then lowered to about 200° C. and a fluoriding agent, such as HF, or other vaporizable fluorine containing compounds such as HF, $SF_4$, $CCl_3F$, $CCl_2F_3$, $CHF_3$, $CHClF_2$ or $CCl_2FCClF_2$, optionally diluted with an inert gas such as nitrogen, is passed through the reactor. The inert gas or nitrogen can be gradually reduced until only HF or other vaporizable fluorine containing compounds is being passed through the reactor. At this point, the temperature can be increased to about 450° C. and held at that temperature to convert the magnesium oxide to a fluoride content corresponding to at least 40 percent by weight, e.g., for 15 to 300 minutes, depending on the fluoriding agent flowrate and the catalyst volume. The fluorides are in the form of magnesium fluoride or magnesium oxyfluoride; the remainder of the catalyst is magnesium oxide. It is understood in the art that fluoriding conditions such as time and temperature can be adjusted to provide higher than 40 percent by weight fluoride-containing material.

Another suitable procedure for the catalyst preparation is to add ammonium hydroxide to a solution of magnesium nitrate and, if present, zinc nitrate and/or aluminum nitrate. The ammonium hydroxide is added to the nitrate solution to a pH of about 9.0 to 9.5. At the end of the addition, the solution is filtered, the solid obtained is washed with water, dried and slowly heated to 500° C., where it is calcined. The calcined product is then treated with a suitable fluorine-containing compound as described above.

Yet another procedure for the preparation of metal (i.e., magnesium, optionally containing also zinc and/or aluminum) fluoride catalysts containing one or more metal fluorides is to treat an aqueous solution of the metal(s) halide(s) or nitrate(s) in deionized water with 48 percent aqueous HF with stirring. Stirring is continued overnight and the slurry evaporated to dryness on a steam bath. The dried solid is then calcined in air at 400° C. for about four hours, cooled to room temperature, crushed and sieved to provide material for use in catalyst evaluations.

Additionally, dehydrofluorination catalysts include lanthanum oxide and fluorided lanthanum oxide.

Suitable fluorided lanthanum oxide compositions may be prepared in any manner analogous to those known to the art for the preparation of fluorided alumina. For example, the catalyst composition can be prepared by fluorination of lanthanum oxide.

Suitable catalyst compositions may also be prepared by precipitation of lanthanum as the hydroxide, which is thereafter dried and calcined to form an oxide, a technique well known to the art. The resulting oxide can then be pretreated as described herein.

The catalyst composition can be fluorinated to the desired fluorine content by pretreatment with a fluorine-containing compound at elevated temperatures, e.g., at about 200° C. to about 450° C. The pretreatment with a vaporizable fluorine-containing compound such as HF, $SF_4$, $CCl_3F$, $CCl_2F_3$, $CHF_3$, $CHClF_2$ or $CCl_2FCClF_2$ can be done in any convenient manner including in the reactor which is to be used for carrying out the dehydrofluorination reaction. By vaporizable fluorine-containing compound is meant a fluorine containing compound which, when passed over the catalyst at the indicated conditions, will fluorinate the catalyst to the desired degree.

A suitable catalyst may be prepared, for example, by drying $La_2O_3$ until essentially all moisture is removed, e.g., for about 18 hours at about 400° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and the vaporizable fluorine-containing compound is passed through the reactor. If necessary, nitrogen or other inert gases can be used as diluents. The $N_2$ or other inert diluents can be gradually reduced until only the vaporizable fluorine-containing compound is being passed through the reactor. At this point the temperature can be increased to about 450° C. and held at that temperature to convert the $La_2O_3$ to a fluorine content corresponding to at least 80 percent $LaF_3$ by weight, e.g., for 15 to 300 minutes, depending on the flow of the fluorine containing compound and the catalyst volume.

Another suitable procedure for the catalyst preparation is to add ammonium hydroxide to a solution of $La(NO_3)_3 6H_2O$. The ammonium hydroxide is added to the nitrate solution to a pH of about 9.0 to 9.5. At the end of the addition, the solution is filtered, the solid obtained is washed with water, and slowly heated to about 400° C., where it is calcined. The calcined product is then treated with a suitable vaporizable fluorine-containing compound as described above.

Additionally, dehydrofluorination catalysts include chromium oxides, fluorided chromium oxides, and cubic chromium trifluoride. Cubic chromium trifluoride may be prepared from $CrF_3 \cdot XH_2O$, where X is 3 to 9, preferably 4, by heating in air or an inert atmosphere (e.g., nitrogen or argon) at a temperature of about 350° C. to about 400° C. for 3 to 12 hours, preferably 3 to 6 hours.

Cubic chromium trifluoride is useful by itself, or together with other chromium compounds, as a dehydrofluorination catalyst. Preparation of cubic chromium trifluoride is described in U.S. Pat. No. 6,031,141, incorporated herein by reference. Of note are catalyst compositions comprising chromium wherein at least 10 weight percent of the chromium is in the form of cubic chromium trifluoride, particularly catalyst compositions wherein at least 25 percent of the chromium is in the form of cubic chromium trifluoride, and especially catalyst compositions wherein at least 60 percent of the chromium is in the form of cubic chromium trifluoride. The chromium, including the cubic chromium trifluoride can be supported on and/or physically mixed with materials such as carbon, aluminum fluoride, fluorided alumina, lanthanum fluoride, magnesium fluoride, calcium fluoride, zinc fluoride and the like. Preferred are combinations including cubic chromium trifluoride in combination with magnesium fluoride and/or zinc fluoride.

Additionally, dehydrofluorination catalysts include activated carbon, or three dimensional matrix carbonaceous materials as disclosed in U.S. Pat. No. 6,369,284, incorporated herein by reference; or carbon or metals such as sodium, potassium, rubidium, cesium, yttrium, lanthanum, cerium, praseodymium, neodymium, samarium, chromium, iron, cobalt, rhodium, nickel, copper, zinc, and mixtures thereof, supported on carbon as disclosed in U.S. Pat. No. 5,268,122, incorporated herein by reference. Carbon from any of the following sources are useful for the process of this invention; wood, peat, coal, coconut shells, bones, lignite, petroleum-based residues and sugar. Commercially available carbons which may be used include those sold under the following trademarks: Barneby & Sutcliffe™, Darco™, Nucharm, Columbia JXN™, Columbia LCK™, Calgon PCB, Calgon BPL™, Westvaco™, Norit™, and Barnaby Cheny NB™.

Carbon includes acid-washed carbon (e.g., carbon which has been treated with hydrochloric acid or hydrochloric acid followed by hydrofluoric acid). Acid treatment is typically sufficient to provide carbon that contains less than 1000 ppm of ash. Suitable acid treatment of carbon is described in U.S. Pat. No. 5,136,113, incorporated herein by reference. The carbon also includes three dimensional matrix porous carbonaceous materials. Examples are those described in U.S. Pat. No. 4,978,649, incorporated herein by reference. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

The physical shape of the catalyst is not critical and may, for example, include pellets, powders or granules. Additionally, for catalysts supported on carbon, the carbon may be in the form of powder, granules, or pellets, or the like. Although not essential, catalysts that have not been fluorided may be treated with HF before use. It is thought that this converts some of the surface oxides to oxyfluorides. This pretreatment can be accomplished by placing the catalyst in a suitable container (which can be the reactor to be used to perform the reaction of the instant invention) and thereafter, passing HF over the dried catalyst so as to partially saturate the catalyst with HF. This is conveniently carried out by passing HF over the catalyst for a period of time (e.g., about 15 to 300 minutes) at a temperature of, for example, about 200° C. to about 450° C.

The catalytic dehydrofluorination may be suitably conducted at a temperature in the range of from about 200° C. to about 500° C., and, in another embodiment, from about 300° C. to about 450° C. The contact time is typically from about 1 to about 450 seconds, and, in another embodiment, from about 10 to about 120 seconds.

The reaction pressure can be subatmospheric, atmospheric or superatmostpheric. Generally, near atmospheric pressures are preferred. However, the dehydrofluorination can be beneficially run under reduced pressure (i.e., pressures less than one atmosphere).

The catalytic dehydrofluorination can optionally be carried out in the presence of an inert gas such as nitrogen, helium, or argon. The addition of an inert gas can be used to increase the extent of dehydrofluorination. Of note are processes where the mole ratio of inert gas to hydrofluorocarbon undergoing dehydrofluorination is from about 5:1 to about 1:1. Nitrogen is the preferred inert gas.

A further aspect provides a process for the manufacture of a hydrofluoroolefin by dehydrofluorination of a hydrofluorocarbon in a reaction zone at elevated temperature in the absence of catalyst.

In the present embodiment of dehydrofluorination, the dehydrofluorination of hydrofluorocarbon can be carried out in a reaction zone at an elevated temperature in the absence of a catalyst as described below in the description for the pyrolysis of $CF_3CH_2CF_3$ to $CF_2=CHCF_3$ and HF. Appropriate temperatures may be between about 350° C. and about 900° C., and, in another embodiment, between about 450° C. and about 900° C. The residence time of gases in the reaction zone is typically from about 0.5 to about 60 seconds, and, in another embodiment, from about 2 seconds to about 20 seconds.

The reaction pressure for the dehydrofluorination reaction at elevated temperature in the absence of catalyst may be subatmospheric, atmospheric, or superatmospheric. Generally, near atmospheric pressures are preferred. However, the dehydrofluorination can be beneficially run under reduced pressure (i.e., pressures less than one atmosphere).

The dehydrofluorination at an elevated temperature in the absence of a catalyst may optionally be carried out in the presence of an inert gas such as nitrogen, helium or argon. The addition of an inert gas can be used to increase the extent of dehydrofluorination. Of note are processes where the mole ratio of inert gas to the hydrofluorocarbon undergoing dehydrofluorination is from about 5:1 to about 1:1. Nitrogen is the preferred inert gas.

The reaction zone for either catalyzed or non-catalyzed dehydrofluorination may be a reaction vessel fabricated from nickel, iron, titanium or their alloys, as described in U.S. Pat. No. 6,540,933, incorporated herein by reference. A reaction vessel of these materials (e.g., a metal tube) optionally packed with the metal in suitable form may also be used. When reference is made to alloys, it is meant a nickel alloy containing from about 1 to about 99.9 weight percent nickel, an iron alloy containing about 0.2 to about 99.8 weight percent iron, and a titanium alloy containing about 72 to about 99.8 weight percent titanium. Of note is the use of an empty (unpacked) reaction vessel made of nickel or alloys of nickel such as those containing about 40 weight percent to about 80 weight percent nickel, e.g., Inconel™ 600 nickel alloy, Hastelloy™ C617 nickel alloy or Hastelloy™ C276 nickel alloy.

When used for packing, the metal or metal alloys may be particles or formed shapes such as, for example, perforated plates, rings, wire, screen, chips, pipe, shot, gauze, or wool.

The product mixture resulting from the dehydrofluorination of hydrofluorocarbon will contain hydrofluoroolefin, unreacted hydrofluorocarbon and hydrogen fluoride. The amount of unreacted hydrofluorocarbon will depend upon the percent conversion achieved in the reaction.

It has been discovered and is disclosed in co-owned, co-pending U.S. patent application Ser. Nos. 11/590,343 and 11/590,448, filed Oct. 30, 2006; Ser. Nos. 11/590,457, 11/590,454, and 11/590,455, filed Oct. 31, 2006; and Ser. No. 11/264,209, filed Nov. 1, 2005, that hydrofluoroolefins may form azeotrope or near-azeotrope compositions with hydrogen fluoride. These azeotrope and near-azeotrope compositions are useful in processes to produce hydrofluoroolefins and in processes to separate hydrofluoroolefins from hydrogen fluoride and hydrofluorocarbons.

As recognized in the art, an azeotrope or a near-azeotrope composition is an admixture of two or more different components which, when in liquid form under a given pressure, will boil at a substantially constant temperature, which temperature may be higher or lower than the boiling temperatures of the individual components, and which will provide a vapor composition essentially identical to the liquid composition undergoing boiling.

For the purpose of this discussion, near-azeotrope composition (also commonly referred to as an "azeotrope-like composition") means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-near-azeotrope compositions in which during boiling or evaporation, the liquid composition changes to a substantial degree.

Additionally, near-azeotrope compositions exhibit dew point pressure and bubble point pressure with virtually no pressure differential. That is to say that the difference in the dew point pressure and bubble point pressure at a given temperature will be a small value. It may be stated that compositions with a difference in dew point pressure and bubble point pressure of less than or equal to 3 percent (based upon the bubble point pressure) may be considered to be a near-azeotrope.

Accordingly, the essential features of an azeotrope or a near-azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope or near-azeotrope liquid composition is subjected to boiling at different pressures. Thus, an azeotrope or a near-azeotrope composition may be defined in terms of the unique relationship that exists among the components or in terms of the compositional ranges of the components or in terms of exact weight percentages of each component of the composition characterized by a fixed boiling point at a specified pressure.

It should be understood that while an azeotrope or near-azeotrope composition may exist at a particular ratio of the components at given temperatures and pressures, the azeotrope composition may also exist in compositions containing other components. These additional components include the individual components of the azeotrope composition, said components being present as an excess above the amount being present as the azeotrope composition. For example, the azeotrope of a hydrofluoroolefin and hydrogen fluoride may be present in a composition that has an excess of said hydrofluoroolefin, meaning that the azeotrope composition is present and additional hydrofluoroolefin is also present. Also for example, the azeotrope of a hydrofluoroolefin and hydrogen fluoride as well as an azeotrope of the starting hydrofluorocarbon and hydrogen fluoride may be present in a composition that has an excess of the starting hydrofluorocarbon used for the dehydrofluorination reaction to produce said hydrofluoroolefin, meaning that the azeotrope composition is present and additional starting hydrofluorocarbon is also present. For instance, the azeotrope of HFC-1225ye ($CF_3CF=CHF$) and hydrogen fluoride may be present in a composition that has an excess of HFC-1225ye, meaning that the azeotrope composition is present and additional HFC-1225ye is also present. Also, for example, the azeotrope of HFC-1225ye ($CF_3CF=CHF$) and hydrogen fluoride may be present in a composition that has an excess of a suitable starting hydrofluorocarbon for the dehydrofluorination reaction, such as HFC-236ea, meaning that the azeotrope composition is present and additional HFC-236ea is also present.

It has been discovered that both hydrofluoroolefins and hydrofluorocarbons may form azeotrope compositions with hydrogen fluoride. Generally, the hydrofluoroolefin/hydrogen fluoride azeotrope composition will boil at a lower temperature than the corresponding precursor hydrofluorocarbon/hydrogen fluoride azeotrope composition. Thus, it should be possible to separate the hydrofluoroolefin/hydrogen fluoride azeotrope from the hydrofluorocarbon/hydrogen fluoride azeotrope, or to separate the hydrofluoroolefin/hydrogen fluoride azeotrope from the hydrofluorocarbon by azeotropic distillation.

The present process to produce hydrofluoroolefin may further comprise the step of distilling the product mixture to produce a distillate composition comprising an azeotrope composition containing hydrofluoroolefin and hydrogen fluoride.

The distillation step may additionally provide a column bottoms composition comprising unconverted hydrofluorocarbon used in the dehydrofluorination reaction. There may additionally be some amount of hydrogen fluoride present in the column bottoms composition. The amount of hydrogen fluoride in the hydrofluorocarbon from the bottom of the distillation column may vary from about 50 mole percent to less than 1 part per million (ppm, mole basis) depending on the manner in which the dehydrofluorination reaction is conducted.

One embodiment for operating the present distillation involves providing an excess of hydrofluoroolefin to the distillation column. If the proper amount of hydrofluoroolefin is fed to the column, then all the hydrogen fluoride may be taken overhead as an azeotrope composition containing hydrofluoroolefin and hydrogen fluoride. Thus, the hydrofluorocarbon removed from the column bottoms will be essentially free of hydrogen fluoride.

As described herein, by "essentially free of hydrogen fluoride" is meant that the composition contains less than about 100 ppm (mole basis), preferably less than about 10 ppm and most preferably less than about 1 ppm, of hydrogen fluoride.

A further aspect provides a process for the separation of a hydrofluoroolefin from a hydrofluorocarbon wherein said hydrofluoroolefin contains one less fluorine atom and one less hydrogen atom than said hydrofluorocarbon, said process comprising forming a mixture comprising hydrofluoroolefin, hydrofluorocarbon and hydrogen fluoride; and subjecting said mixture to a distillation step forming a column distillate composition comprising an azeotrope or near-azeotrope composition of hydrogen fluoride and hydrofluoroolefin essentially free of said hydrofluorocarbon.

As described herein, by "essentially free of said hydrofluorocarbon" is meant that the composition contains less than about 100 ppm (mole basis), preferably less than about 10 ppm and most preferably less than about 1 ppm, of hydrofluorocarbon.

The present process to separate a hydrofluoroolefin from a hydrofluorocarbon may further form a column bottoms composition comprising hydrofluorocarbon used in the dehydrofluorination reaction. The column bottoms composition comprising hydrofluorocarbon may contain some amount of hydrogen fluoride. The amount of hydrogen fluoride in the hydrofluorocarbon from the bottom of the distillation column may vary from about 50 mole percent to less than 1 part per million (ppm, mole basis) depending on the manner in which the dehydrofluorination reaction is conducted.

One embodiment for operating the present distillation involves providing an excess of hydrofluoroolefin to the distillation column. If the proper amount of hydrofluoroolefin is fed to the column, then all the hydrogen fluoride may be taken overhead as an azeotrope composition containing hydrofluoroolefin and hydrogen fluoride. Thus, the hydrofluorocarbon removed from the column bottoms will be essentially free of hydrogen fluoride.

In the distillation step, the distillate composition exiting the distillation column overhead comprising hydrogen fluoride and hydrofluoroolefin may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step depend upon a number of parameters, such as the diameter of the distillation column, feed points, and the number of separation stages in the column, among others. The operating pressure of the distillation column may range from about 10 psi pressure to about 300 psi (1380 kPa), normally about 20 psi to about 75 psi. The distillation column is typically operated at a pressure of about 25 psi (172 kPa). Normally, increasing the reflux ratio results in increased distillate stream purity, but generally the reflux ratio ranges between 0.2/1 to 200/1. The temperature of the condenser, which is located adjacent to the top of the column, is normally sufficient to substantially fully condense the distillate that is exiting from the top of the column, or is that temperature required to achieve the desired reflux ratio by partial condensation.

The column distillate composition comprising an azeotrope or near-azeotrope composition of hydrogen fluoride and hydrofluoroolefin, essentially free of hydrofluorocarbon, may be treated to remove the hydrogen fluoride and provide pure hydrofluoroolefin as product. This may be accomplished, for example, by neutralization. However, the production of substantial amounts of scrubbing discharge can create aqueous waste disposal concerns. Thus, there remains a need for more efficient, economical and environmentally viable processes to remove hydrogen fluoride from this mixture.

It has been discovered that hydrofluoroolefins may be separated from mixtures of hydrofluoroolefins and hydrogen fluoride by a distillation process that takes advantage of changing azeotrope concentrations at different temperatures and pressures.

Another aspect provides a process for the separation of a hydrofluoroolefin from a mixture comprising an azeotrope or near-azeotrope composition of said hydrofluoroolefin and hydrogen fluoride, said process comprising: a) subjecting said mixture to a first distillation step in which a composition enriched in either (i) hydrogen fluoride or (ii) hydrofluoroolefin is removed as a first distillate composition with a first bottoms composition being enriched in the other of said components (i) or (ii); and b) subjecting said first distillate composition to a second distillation step conducted at a different pressure in which the component enriched as first bottoms composition in (a) is removed as a second distillate composition with the bottoms composition of the second distillation step enriched in the same component which was enriched in the first distillate composition.

The first column bottoms composition comprising hydrofluoroolefin may be produced to be essentially free of hydrogen fluoride. Additionally, the second column bottoms sample comprising hydrogen fluoride may be produced to be essentially free of hydrofluoroolefin.

As described herein, by "essentially free of hydrofluoroolefin" is meant that the composition contains less than about 100 ppm (mole basis), preferably less than about 10 ppm and most preferably less than about 1 ppm, of hydrofluoroolefin.

The process as described above takes advantage of the change in azeotrope composition at different pressures to effectuate the separation of hydrofluoroolefin and hydrogen fluoride. The first distillation step may be carried out at high pressure relative to the second distillation step. At higher pressures, the hydrogen fluoride/hydrofluoroolefin azeotrope contains less hydrofluoroolefin. Thus, this high-pressure distillation step produces an excess of hydrofluoroolefin, which boiling at a higher temperature than the azeotrope will exit the column as the column bottoms composition comprising hydrofluoroolefin. The first column distillate composition is then fed to a second distillation step operating at lower pressure. At the lower pressure, the hydrogen fluoride/hydrofluoroolefin azeotrope shifts to lower concentrations of hydrogen fluoride. Therefore, in this second distillation step, there exists an excess of hydrogen fluoride. The excess hydrogen fluoride, having a boiling point higher than the azeotrope, exits the second distillation column as the column bottoms composition comprising hydrogen fluoride.

The reverse of the process described in the preceding paragraph is also possible. The first distillation step may be carried out at a lower pressure relative to the second distillation step. At lower pressure, the hydrogen fluoride/hydrofluoroolefin azeotrope contains less hydrogen fluoride. Thus, this low-pressure distillation step produces an excess of hydrogen fluoride, which boiling at a higher temperature than the azeotrope will exit the column as the bottoms composition comprising hydrogen fluoride. The first column distillate composition is then fed to a second distillation step operating at higher pressure. At the higher pressure, the hydrogen fluoride/hydrofluoroolefin azeotrope shifts to higher concentrations of hydrogen fluoride. Therefore, in this second distillation step, there exists an excess of hydrofluoroolefin. The excess hydrofluoroolefin, having a boiling point higher than the azeotrope, exits the second distillation column as the bottoms composition.

In general, the dehydrofluorination of hydrofluorocarbons is an endothermic reaction and thus may be accomplished in a tubular reactor with catalyst in the tubes and with a heating medium on the shellside of the reactor. Alternatively, a heat carrier may be used to permit adiabatic operation. Either essentially pure hydrofluorocarbon or essentially pure hydrofluoroolefin, both being produced by the distillation processes described herein, may be recycled back to the reactor to serve as heat carrier. Hydrofluorocarbon is a preferred heat carrier, as introduction of hydrofluoroolefin to the dehydrofluorination reactor will result in a reduction in single-pass conversion of hydrofluorocarbon.

In both the first and second distillation steps, the distillate exiting the distillation column overhead comprising hydrogen fluoride and hydrofluoroolefin may be condensed using, for example, standard reflux condensers. At least a portion of this condensed stream may be returned to the top of the column as reflux. The specific conditions which may be used for practicing the distillation steps depend upon a number of parameters, such as the diameter of the distillation column, feed points, and the number of separation stages in the column, among others. The operating pressure of the first distillation column may range from about 50 psi (345 kPa) pressure to about 225 psi (1550 kPa), normally about 50 psi (345 kPa) to about 100 psi (690 kPa). The first distillation column is typically operated at a pressure of about 75 psi (520 kPa). Normally, increasing the reflux ratio results in increased distillate stream purity, but generally the reflux ratio ranges between 0.1/1 to 100/1. The temperature of the condenser, which is located adjacent to the top of the column, is normally sufficient to substantially fully condense the distillate that is exiting from the top of the column, or is that temperature required to achieve the desired reflux ratio by partial condensation.

The operating pressure of the second distillation column may range from about 5 psi (34 kPa) pressure to about 50 psi (345 kPa), normally about 5 psi (34 kPa) to about 20 psi (138 kPa). The second distillation column is typically operated at a pressure of about 17 psi (117 kPa). Normally, increasing the reflux ratio results in increased distillate stream purity, but generally the reflux ratio ranges between 0.1/1 to 50/1. The temperature of the condenser, which is located adjacent to the top of the column, is normally sufficient to substantially fully condense the distillate that is exiting from the top of the column, or is that temperature required to achieve the desired reflux ratio by partial condensation.

Figure 1:
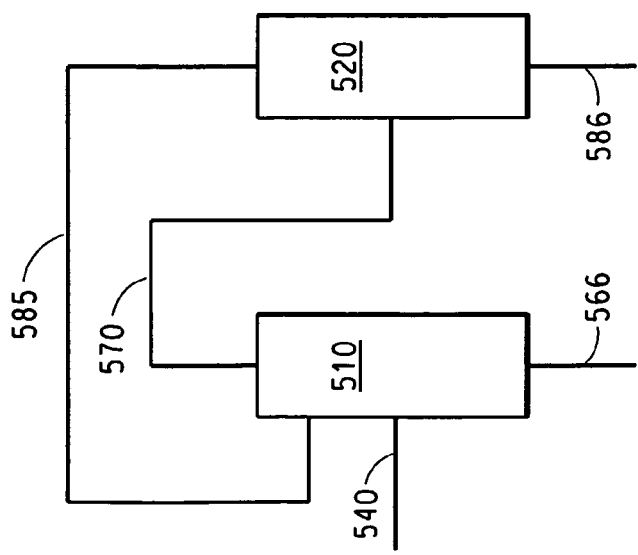
FIG. 1 is a schematic flow diagram illustrating one embodiment for practicing a two-column azeotropic distillation process.

FIG. 1 is illustrative of one embodiment for practicing the present two-column distillation process for the separation of hydrofluoroolefin and hydrogen fluoride. Referring to FIG. 1, a feed mixture derived from a prior azeotropic distillation comprising hydrogen fluoride and hydrofluoroolefin, is passed through line (540) to a multiple stage distillation column (510), operating at a temperature of about 77° C. and a pressure of about 335 psi (2310 kPa). The bottoms of the distillation column (510), containing essentially pure hydrofluoroolefin at a temperature of about 86° C. and a pressure of about 337 psi (2320 kPa) is removed from the bottom of column (510) through line (566). The distillate from column (510), containing the hydrogen fluoride/hydrofluoroolefin azeotrope at a temperature of about 77° C. and a pressure of about 335 psi (2310 kPa) is removed from the top of column (510) and sent through line (570) to a multiple stage distillation column (520). The distillate from column (520), containing the hydrogen fluoride/hydrofluoroolefin azeotrope at a temperature of about −19° C. and a pressure of about 17 psi (117 kPa), is removed from column (520) through line (585) and is recycled back to column (510). The bottoms of column (520) containing essentially pure hydrogen fluoride at a temperature of about 26° C. and a pressure of about 19 psi (131 kPa) is removed through line (586).

A further aspect provides a process for the purification of hydrofluoroolefin from a mixture of hydrofluoroolefin, hydrofluorocarbon, and hydrogen fluoride, said process comprising: a) subjecting said mixture to a first distillation step to form a first distillate composition comprising an azeotrope or near-azeotrope composition containing hydrofluoroolefin and hydrogen fluoride and a first bottoms composition comprising hydrofluorocarbon; b) subjecting said first distillate to a second distillation step from which a composition enriched in either (i) hydrogen fluoride or (ii) hydrofluoroolefin is removed as a second distillate composition with a second bottoms composition being enriched in the other of said components (i) or (ii); and c) subjecting said second distillate composition to a third distillation step conducted at a different pressure than the second distillation step in which the component enriched in the second bottoms composition in (b) is removed as a third distillate composition with a third bottoms composition enriched in the same component that was enriched in the second distillate composition.

The present method may optionally further comprise recycling at least some portion of said second bottoms composition (hydrofluoroolefin) to said first distillation step. The recycle of hydrofluoroolefin will ensure that all the hydrogen fluoride is taken overhead as the azeotrope composition with the hydrofluoroolefin. Thus, the hydrofluorocarbon exiting the process as the first column bottoms composition may be produced to be essentially free of hydrogen fluoride and hydrofluoroolefin. The hydrofluoroolefin exiting the process as the second column bottoms composition may be produced to be essentially free of hydrogen fluoride. The hydrogen fluoride exiting the process as the third column bottoms composition may be produced to be essentially free of hydrofluoroolefin.

As described herein, by "essentially free of hydrogen fluoride and hydrofluoroolefin" is meant that the composition contains less than about 100 ppm (mole basis), preferably less than about 10 ppm and most preferably less than about 1 ppm, of each of hydrogen fluoride and hydrofluoroolefin.

The conditions for the first distillation step are the same as those for the azeotropic distillation process for separation of hydrofluoroolefin from hydrofluorocarbon, described earlier herein. The conditions for the second and third distillation steps are the same as the conditions for the 2 column process for separation of hydrofluoroolefin from hydrogen fluoride, also described earlier herein.

A further aspect provides a process to produce hydrofluoroolefin comprising: a) feeding hydrofluorocarbon containing at least one hydrogen and at least one fluorine on adjacent carbons to a reaction zone for dehydrofluorination to form a reaction product composition comprising hydrofluoroolefin, unreacted hydrofluorocarbon and hydrogen fluoride; b) subjecting said reaction product composition to a first distillation step to form a first distillate composition comprising an azeotrope or near-azeotrope composition containing hydrofluoroolefin and hydrogen fluoride and a first bottoms composition comprising hydrofluorocarbon; c) subjecting said first distillate composition to a second distillation step from which a composition enriched in either (i) hydrogen fluoride or (ii) hydrofluoroolefin is removed as a second distillate composition with a second bottoms composition being enriched in the other of said components (i) or (ii); and d) subjecting said second distillate composition to a third distillation step conducted at a different pressure than the second distillation step in which the component enriched in the second bottoms composition in (c) is removed as a third distillate composition with a third bottoms composition enriched in the same component that was enriched in the second distillate composition.

Optionally, the process may further comprise recycling at least some portion of said first bottoms composition (hydrofluorocarbon) to said reaction zone. Optionally, the process may further comprise recycling at least some portion of said second bottoms composition or said third bottoms composition (i.e. that which is hydrofluoroolefin) to said reaction zone. Optionally, the process may further comprise recycling at least some portion of said second bottoms composition or said third bottoms composition (i.e. that which is hydrofluoroolefin) to said first distillation step. Optionally, the process may further comprise recovering at least some portion of said second bottoms composition or said third bottoms composition as hydrofluoroolefin essentially free of hydrofluorocarbon and hydrogen fluoride.

As described herein, by "essentially free of hydrofluorocarbon and hydrogen fluoride" is meant that the composition contains less than about 100 ppm (mole basis), preferably less than about 10 ppm and most preferably less than about 1 ppm, of each of hydrofluorocarbon and hydrogen fluoride.

FIG. 2 is illustrative of one embodiment for practicing the present process for production of hydrofluoroolefin. Hydrofluorocarbon is fed through line (360) to reactor (320). The reactor effluent mixture comprising hydrogen fluoride, hydrofluorocarbon and hydrofluoroolefin, exits the reactor through line (450) and is fed to a multiple stage distillation column (410). The bottoms of distillation column (410), containing essentially pure hydrofluorocarbon is removed from the bottom of column (410) through line (466) and may be recycled back to the reactor. The distillate from column (410), containing the hydrogen fluoride/hydrofluoroolefin azeotrope is removed from the top of column (410) and is sent through line (540) to a second multiple stage distillation column (510). The bottoms from column (510), which is essentially pure hydrofluoroolefin, is removed from column (510) through line (566) and may be recycled back to the reactor (320) as a heat carrier. The distillate from column (510), containing the hydrogen fluoride/hydrofluoroolefin azeotrope, is fed through line (570) to a third multiple stage distillation column (520). The distillate from column (520) comprising hydrogen fluoride/hydrofluoroolefin is removed through line (585) and may be recycled to the second distillation column (510). The bottoms composition from column (520) is essentially pure hydrogen fluoride and is removed from column (520) through line (586). The essentially pure hydrogen fluoride product from this process may be used in any manner appropriate such as feeding to a fluorination reactor for production of a fluorochemical compound, or may be neutralized for disposal.

While not illustrated in the Figures, it is understood that certain pieces of process equipment may be used in the processes described herein, for optimization. For instance, pumps, heaters or coolers may be used where appropriate. As an example, it is desirable to have the feed to a distillation column at the same temperature as the point in the column that it is fed. Therefore, heating or cooling of the process stream may be necessary to match the temperature.

Another embodiment provides a process of producing $CF_3CH=CF_2$ by pyrolysis of $CF_3CH_2CF_3$. The process may be written as:

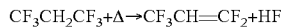

where $\Delta$ represents heat and HF is hydrogen fluoride.

Pyrolysis, as the term is used herein, means chemical change produced by heating in the absence of catalyst. Pyrolysis reactors generally comprise three zones: a) a preheat zone, in which reactants are brought close to the reaction temperature; b) a reaction zone, in which reactants reach reaction temperature and are at least partially pyrolyzed, and products and any byproducts form; c) a quench zone, in which the stream exiting the reaction zone is cooled to stop the pyrolysis reaction. Laboratory-scale reactors have a reaction zone, but the preheating and quenching zones may be omitted.

In this embodiment, the reactor may be of any shape consistent with the process but is preferably a cylindrical tube, either straight or coiled. Although not critical, such reactors typically have an inner diameter of from about 1.3 to about 5.1 cm (about 0.5 to about 2 inches). Heat is applied to the outside of the tube, the chemical reaction taking place on the inside of the tube. The reactor and its associated feed lines, effluent lines and associated units should be constructed, at least as regards the surfaces exposed to the reaction reactants and products, of materials resistant to hydrogen fluoride. Typical materials of construction, well-known to the fluorination art, include stainless steels, in particular of the austenitic type, the well-known high nickel alloys, such as Monel® nickel-copper alloys, Hastelloy-based alloys and Inconel® nickel-chromium alloys and copper clad steel. Where the reactor is exposed to high temperature the reactor may be constructed of more than one material. For example, the outer surface layer of the reactor should be chosen for ability to maintain structural integrity and resist corrosion at the pyrolysis temperature, the inner surface layer of the reactor should be chosen of materials resistant to attack by, that is, inert to, the reactant and products. In the case of the present process, the product hydrogen fluoride is corrosive to certain materials. In other words, the reactor may be constructed of an outer material chosen for physical strength at high temperature and an inner material chosen for resistance to corrosion by the reactants and products under the temperature of the pyrolysis.

For the process of this embodiment, it is preferred that the reactor inner surface layer be made of high nickel alloy, that is an alloy containing at least about 50 wt % nickel, preferably a nickel alloy having at least about 75 wt % nickel, more preferably a nickel alloy having less than about 8 wt % chromium, still more preferably a nickel alloy having at least about 98 wt % nickel, and most preferably substantially pure nickel, such as the commercial grade known as Nickel 200. More preferable than nickel or its alloys as the material for the inner surface layer of the reactor is gold. The thickness of the inner surface layer does not substantially affect the pyrolysis and is not critical so long as the integrity of the inner surface layer is intact. The thickness of the inner surface layer is typically from about 10 to about 100 mils (0.25 to 2.5 mm). The thickness of the inner surface layer can be determined by the method of fabrication, the cost of materials, and the desired reactor life.

The reactor outer surface layer is resistant to oxidation or other corrosion and maintains sufficient strength at the reaction temperatures to keep the reaction vessel from failing of distorting. This layer is preferably Inconel® alloy, more preferably Inconel® 600.

The present pyrolysis of $CF_3CH_2CF_3$ to $CF_2=CHCF_3$ and HF is carried out in the absence of catalyst in a substantially empty reactor. By absence of catalyst is meant that no material or treatment is added to the pyrolysis reactor that increases the reaction rate by reducing the activation energy of the pyrolysis process. It is understood that although surfaces that are unavoidably present in any containment vessel, such as a pyrolysis reactor, may have incidental catalytic or anticatalytic effects on the pyrolysis process, the effect makes an insignificant contribution, if any, to the pyrolysis rate. More specifically, absence of catalyst means absence of conventional catalysts having high surface area in a particulate, pellet, fibrous or supported form that are useful in promoting the elimination of hydrogen fluoride from a hydrofluorocarbon (i.e., dehydrofluorination). Example, dehydrofluorination catalysts include: chromium oxide, optionally containing other metals, metal oxides or metal halides; chromium fluoride, unsupported or supported; and activated carbon, optionally containing other metals, metal oxides or metal halides.

Substantially empty reactors useful for carrying out the present process are tubes comprising the aforementioned materials of construction. Substantially empty reactors include those wherein the flow of gases through the reactor is partially obstructed to cause back-mixing, i.e. turbulence, and thereby promote mixing of gases and good heat transfer. This partial obstruction can be conveniently obtained by placing packing within the interior of the reactor, filling its cross-section or by using perforated baffles. The reactor packing can be particulate or fibrillar, preferably in cartridge disposition for ease of insertion and removal, has an open structure like that of Raschig Rings or other packings with a high free volume, to avoid the accumulation of coke and to minimize pressure drop, and permits the free flow of gas. Preferably the exterior surface of such reactor packing comprises materials identical to those of the reactor inner surface layer; materials that do not catalyze dehydrofluorination of hydrofluorocarbons and are resistant to hydrogen fluoride. The free volume is the volume of the reaction zone minus the volume of the material that makes up the reactor packing. The free volume is at least about 80%, preferably at least about 90%, and more preferably about 95%.

The pyrolysis which accomplishes the conversion of $CF_3CH_2CF_3$ to $CF_2=CHCF_3$ is suitably conducted at a temperature of at least about 700° C., preferably at least about 750° C., and more preferably at least about 800° C. The maximum temperature is no greater than about 1,000° C., preferably no greater than about 950° C., and more preferably no greater than about 900° C. The pyrolysis temperature is the temperature of the gases inside at about the mid-point of the reaction zone.

The residence time of gases in the reaction zone is typically from about 0.5 to about 60 seconds, more preferably from about 2 seconds to about 20 seconds at temperatures of from about 700 to about 900° C. and atmospheric pressure. Residence time is determined from the net volume of the reaction zone and the volumetric feed rate of the gaseous feed to the reactor at a given reaction temperature and pressure, and refers to the average amount of time a volume of gas remains in the reaction zone.

The pyrolysis is preferably carried out to a conversion of the $CF_3CH_2CF_3$ at least about 25%, more preferably to at least about 35%, and most preferably to at least about 45%. By conversion is meant the portion of the reactant that is consumed during a single pass through the reactor. Pyrolysis is preferably carried out to a yield of $CF_3CH=CF_2$ of at least about 50%, more preferably at least about 60%, and most preferably at least about 75%. By yield is meant the moles of $CF_3CH=CF_2$ produced per mole of $CF_3CH_2CF_3$ consumed.

The reaction is preferably conducted at subatmospheric, or atmospheric total pressure. That is, the reactants plus other ingredients are at subatmospheric pressure or atmospheric pressure. (If inert gases are present as other ingredients, as discussed below, the sum of the partial pressures of the reactants plus such ingredients is subatmospheric or atmospheric). Near atmospheric total pressure is more preferred. The reaction can be beneficially run under reduced total pressure (i.e., total pressure less than one atmosphere).

The reaction according to this embodiment can be conducted in the presence of one or more unreactive diluent gases, that is diluent gases that do not react under the pyrolysis conditions. Such unreactive diluent gases include the inert gases nitrogen, argon, and helium. Fluorocarbons that are stable under the pyrolysis conditions, for example, trifluoromethane and perfluorocarbons, may also be used as unreactive diluent gases. It has been found that inert gases can be used to increase the conversion of $CF_3CH_2CF_3$ to $CF_3CH=CF_2$. Of note are processes where the mole ratio of inert gas to $CF_3CH_2CF_3$ fed to the pyrolysis reactor is from about 5:1 to 1:1. Nitrogen is a preferred inert gas because of its comparatively low cost.

The present process produces a 1:1 molar mixture of HF and $CF_3CH=CF_2$ in the reactor exit stream. The reactor exit stream can also contain unconverted reactant, $CF_3CH_2CF_3$. The components of the reactor exit stream can be separated by conventional means, such as distillation. Hydrogen fluoride and $CF_3CH=CF_2$ form a homogenous low-boiling azeotrope containing about 60 mole percent $CF_3CH=CF_2$. The present process reactor exit stream can be distilled and the low-boiling HF and $CF_3CH=CF_2$ azeotrope taken off as a distillation column overhead stream, leaving substantially pure $CF_3CH_2CF_3$ as a distillation column bottom stream. Recovered $CF_3CH_2CF_3$ reactant may be recycled to the reactor. $CF_3CH=CF_2$ can be separated from its azeotrope with HF by conventional procedures, such as pressure swing distillation or by neutralization of the HF with caustic.

Without further elaboration, it is believed that one skilled in the art can, using the description herein, utilize the disclosed compositions and processes to their fullest extent. The following exemplary embodiments are, therefore, to be construed as merely illustrative, and do not constrain the remainder of the disclosure in any way whatsoever.

EXAMPLES

Example 1

Dehydrofluorination of $CF_3CH_2CHF_2$ to $CF_3CH=CHF$ (E and Z Isomers) Over Carbonaceous Catalyst A Hastelloy™ nickel alloy reactor (2.54 cm OD×2.17 cm ID×24.1 cm L) was charged with 14.32 g (25 mL) of spherical (8 mesh) three dimensional matrix porous carbonaceous material prepared substantially as described in U.S. Pat. No. 4,978,649, incorporated herein by reference. The packed portion of the reactor was heated by a 5"×1" ceramic band heater clamped to the outside of the reactor. A thermocouple positioned between the reactor wall and the heater measured the reactor temperature. After charging the reactor with the carbonaceous material, nitrogen (10 ml/min, $1.7\times10^{-7}$ m$^3$/s) was passed through the reactor and the temperature was raised to 200° C. during a period of one hour and maintained at this temperature for an additional 4 hours. The reactor temperature was then raised to the desired operating temperature and a flow of $CF_3CH_2CHF_2$ and nitrogen was started through the reactor.

A portion of the total reactor effluent was sampled on-line for organic product analysis using a gas chromatograph equipped with a mass selective detector (GC-MS); the results are summarized in Table 3. The bulk of the reactor effluent containing organic products and also inorganic acid, such as HF, was treated with aqueous caustic for neutralization.

TABLE 3

| Reactor Temp. (° C.) | $CF_3CH_2CHF_2$ feed (mL/min) | $N_2$ feed (mL/min) | GC Area Percent | | | |
|---|---|---|---|---|---|---|
| | | | E- $CF_3CH=CHF$ | Z- $CF_3CH=CHF$ | $CF_3CH_2CHF_2$ | Unks |
| 200 | 10 | 20 | 0.1 | ND | 99.6 | 0.3 |
| 250 | 10 | 20 | 0.8 | ND | 99.0 | 0.2 |
| 300 | 10 | 20 | 8.9 | ND | 90.9 | 0.2 |
| 350 | 10 | 10 | 31.6 | 5.7 | 62.3 | 0.4 |
| 350 | 10 | 5 | 42.4 | 8.7 | 48.3 | 0.6 |

ND = not detected

Example 2

Dehydrofluorination of $CF_3CH_2CHF_2$ to $CF_3CH=CHF$ (E and Z Isomers) Over Fluorided Alumina Catalyst A 15 in (38.1 cm)×⅜ in (0.95 cm) Hastelloy tube was charged with 7.96 grams (13 cc) of gamma-alumina ground to 12-20 mesh (0.84 to 1.68 mm). The catalyst was activated by heating at 200° C. for 15 minutes under a nitrogen purge (50 sccm, $8.3\times10^{-7}$ m$^3$/s). The temperature was raised to 325° C. for 10 minutes, to 400° C. for 20 minutes, and then lowered to 300° C. for 60 minutes. The nitrogen flow was reduced to 35 sccm ($5.8\times10^{-7}$ m$^3$/s) and anhydrous HF vapor was fed at 12 sccm ($2.0\times10^{-7}$ m$^3$/s) for 35 minutes. The temperature was then raised to 325° C. for 60 minutes, to 350° C. for 60 minutes, to 375° C. for 90 minutes, to 400° C. for 30 minutes, and to 425° C. for 40 minutes. The nitrogen flow was then reduced to 25 sccm ($4.2\times10^{-7}$ m$^3$/s) and the HF raised to 20 sccm ($3.3\times10^{-7}$ m$^3$/s) for 20 minutes. The nitrogen flow was then reduced to 15 sccm ($2.5\times10^{-7}$ m$^3$/s) and the HF flow increased to 28 sccm ($4.7\times10^{-7}$ m$^3$/s) for 20 minutes. The nitrogen flow was then reduced to 5 sccm ($8.3\times10^{-8}$ m$^3$/s) and the HF increased to 36 sccm ($6.0\times10^{-7}$ m$^3$/s) for 20 minutes. The nitrogen flow was then shut off, and the HF flow increased to 40 sccm ($6.7\times10^{-7}$ m$^3$/s) for 121 minutes.

The temperature of the reactor was set to 375° C., and $CF_3CH_2CHF_2$ was fed at a flow rate of 5.46 mL/hour (20.80 sccm, $3.5\times10^{-7}$ m$^3$) and nitrogen co-fed at a flow rate of 5.2 sccm ($8.7\times10^{-8}$ m$^3$). The effluent was analyzed by GC; the results are summarized in Table 4.

TABLE 4

| Component | GC Area % |
|---|---|
| E-$CF_3CH$=CHF | 71.4 |
| $CF_3CH_2CHF_2$ | 15.2 |
| Z-$CF_3CH$=CHF | 12.1 |
| unknown | 1.3 |

Example 3

Dehydrofluorination of $CF_3CHFCHF_2$ to $CF_3CF$=CHF (E and Z Isomers) Over Carbonaceous Catalyst A mixture of $CF_3CHFCHF_2$ and nitrogen were passed through the reactor following the procedure of Example 1. The results of GC analysis of the reactor effluent are summarized in Table 5.

TABLE 5

| Reactor | | | GC Area Percent | | | |
|---|---|---|---|---|---|---|
| Temp. (° C.) | $CF_3CHFCHF_2$ feed (mL/min) | $N_2$ feed (mL/min) | Z-$CF_3CF$=CHF | E-$CF_3CF$=CHF | $CF_3CHFCHF_2$ | Unks |
| 200 | 10 | 20 | 0.03 | ND | 99.97 | ND |
| 250 | 10 | 20 | 0.2 | 0.03 | 99.8 | ND |
| 300 | 10 | 20 | 1.4 | 0.22 | 98.4 | 0.01 |
| 350 | 10 | 20 | 5.4 | 0.96 | 93.1 | 0.5 |
| 400 | 10 | 20 | 38.1 | 9.0 | 51.7 | 1.1 |
| 400 | 10 | 10 | 37.9 | 8.7 | 51.6 | 1.8 |
| 400 | 10 | 5 | 42.6 | 9.5 | 46.7 | 1.2 |
| 400 | 10 | 40 | 13.2 | 2.5 | 71.6 | 12.7 |

ND = not detected
Unks = unknowns

Example 4

Synthesis of $CF_3CF$=$CH_2$ by Dehydrofluorination with Fluorided Alumina Catalyst A Hastelloy™ tube reactor (2.54 cm OD×2.17 cm ID×24.1 cm L) was filled with 25 cc of gamma-alumina ground to 12-20 mesh (0.84 to 1.68 mm). The catalyst was activated by heating at 200° C. for 15 minutes under a nitrogen purge and then reacted with a HF/$N_2$ mixture heated up to 425° C. to yield 16.7 gm of activated fluorided alumina.

At a temperature of 350° C., 10 sccm of nitrogen ($1.7\times10^{-7}$ m$^3$/s) and 15 sccm ($2.5\times10^{-7}$ m$^3$/s) of $CF_3CF_2CH_3$ were mixed and flowed through the reactor. The temperature was then raised to 400° C., the flow rates held constant. The effluent for both temperatures was sampled and analyzed by $^{19}$F NMR. Additionally, the effluent was analyzed by GC to determine concentrations as listed in Table 6.

TABLE 6

| Temp., ° C. | $N_2$ flow (sccm) | $CF_3CF_2CH_3$ flow (sccm) | Concentrations, (Mole %) | | |
|---|---|---|---|---|---|
| | | | $CF_3CF$=$CH_2$ | $CF_3CF_2CH_3$ | Unks |
| 350 | 10 | 15 | 84.2 | 12.8 | 3.0 |
| 400 | 10 | 15 | 91.3 | 1.9 | 6.8 |

Unks = unknowns

Example 5

Synthesis of $CF_3CF$=$CH_2$ with Carbon Catalyst

Following the procedure of Example 3, a mixture of 10 sccm ($1.7\times10^{-7}$ m$^3$/s) of nitrogen and 15 sccm ($2.5\times10^{-7}$ m$^3$/s) of $CF_3CF_2CH_3$ were passed through the reactor giving a contact time of 60 seconds. The flows were reduced to 5 sccm $8.3\times10^{-8}$ m$^3$/s) of nitrogen (and 7.5 sccm ($1.3\times10^{-7}$ m$^3$/s) of $CF_3CF_2CH_3$ giving a contact time of 120 seconds. The effluent was sampled under both sets of conditions and analyzed by $^{19}$F NMR. The effluent compositions as determined by GC are listed in Table 7.

TABLE 7

| Temp., ° C. | $N_2$ flow (sccm) | $CF_3CF_2CH_3$ flow (sccm) | Concentrations, Mole % | | |
|---|---|---|---|---|---|
| | | | $CF_3CF$=$CH_2$ | $CF_3CF_2CH_3$ | Unks |
| 400 | 10 | 15 | 6.0 | 93.9 | 0.1 |
| 400 | 5 | 7.5 | 22.8 | 76.4 | 0.8 |

Unks = unknowns

Example 6

Synthesis of $CHF_2CF$=CHF from $CHF_2CF_2CH_2F$

A 0.375 inch (0.95 cm) O.D. Hastelloy™ nickel alloy tube was charged with 7.0 grams (10 cc) of gamma-alumina ground to 12/20 mesh (0.84 to 1.68 mm). The tube was purged with nitrogen (50 sccm, $8.3\times10^{-7}$ m$^3$/s) for twenty minutes as the temperature was raised from 40° C. to 175° C. The nitrogen flow was continued as anhydrous hydrogen fluoride (50 sccm, 8.3×10$^{-7}$ m$^3$/s) was added to the reactor for about 1.5 hours. The nitrogen flow was then reduced to 20 sccm (3.3× 10$^{-7}$ m$^3$/s) and the hydrogen fluoride flow increased to 80 sccm (1.3×10$^{-6}$ m$^3$/s) as the temperature in the tube was increased from 174° C. to 373° C. over the course of 3.7 hours. The nitrogen flow was then reduced to 10 sccm (1.7× 10$^{-7}$ m$^3$/s) and the hydrogen fluoride flow was maintained at 80 sccm (1.3×10$^{-6}$ m$^3$/s) for one hour at 400° C. The reactor temperature was then adjusted to 290° C. and the reactor purged with nitrogen.

CHF$_2$CF$_2$CH$_2$F was vaporized and fed to the reactor at such a rate as to maintain a contact time with the catalyst of 120 seconds. No nitrogen co-feed was present. Gas chromatographic analyses of the reactor effluent at three temperatures are listed in Table 8.

M

TABLE 8

| Reactor Temp, ° C. | GC Area Percent | | |
|---|---|---|---|
| | CHF$_2$CF$_2$CH$_2$F | CHF$_2$CHFCHF$_2$ | E and Z-CHF$_2$CF=CHF |
| 275 | 72.3 | 5.5 | 22.0 |
| 325 | 40.8 | 6.9 | 51.7 |
| 375 | 27.0 | 3.2 | 68.9 |

Example 7

Synthesis of CF$_3$CH=CFCF$_3$

A Hastelloy™ nickel alloy reactor (2.54 cm OD×2.17 cm ID×24.1 cm L) was charged with 13.5 g (25 mL) of spherical (8 mesh) three dimensional matrix porous carbonaceous material, as described in Example 1.

At a temperature of 300° C., 12.5 sccm of nitrogen (2.1×10$^{-7}$ m$^3$/s) and 12.5 sccm (2.1×10$^{-7}$ m$^3$/s) of CF$_3$CHFCHFCH$_3$ were mixed and flowed through the reactor. The reactor temperature was raised to 350° C. and finally to 400° C. and the effluent were analyzed by GC/MS at each temperature. The effluent composition is listed in Table 9.

TABLE 9

| Reactor Temp., ° C. | Mole percent | | | | |
|---|---|---|---|---|---|
| | CF$_3$CF=CFCF$_3$ | E- and Z-CF$_3$CH=CFCF$_3$ | CF$_3$CHFCHFCF$_3$ | CF$_3$C≡CCF$_3$ | unknowns |
| 300 | 0.2 | 24.4 | 73.3 | ND | 2.1 |
| 350 | 0.2 | 71.6 | 26.1 | ND | 2.1 |
| 400 | — | 90.1 | 8.3 | 0.4 | 1.2 |

Example 8

Synthesis of CH$_2$=CFCH$_2$CF$_3$ and E/Z—CF$_3$CH=CFCH$_3$

A Hastelloy™ nickel alloy reactor (2.54 cm OD×2.17 cm ID×24.1 cm L) was charged with 13.5 g (25 mL) of spherical (8 mesh) three dimensional matrix porous carbonaceous material, as described in Example 1.

At a temperature of 350° C., 25 sccm of N$_2$ (4.2×10$^{-7}$ m$^3$/s) and 25 sccm (4.2×10$^{-7}$ m$^3$/s) of CF$_3$CH$_2$CF$_2$CH$_3$ were mixed and flowed through the reactor. The effluent was analyzed by GC/MS and the results are listed in Table 10.

TABLE 10

| Component | Mole Percent |
|---|---|
| CH$_2$=CFCH$_2$CF$_3$ | 14.5 |
| E- and Z-CF$_3$CH=CFCH$_3$ | 11.9 |
| CF$_3$CH$_2$CF$_2$CH$_3$ | 72.0 |
| unknowns | 1.6 |

Example 9

Dehydrofluorination of CF$_3$CHFCHFCF$_2$CF$_3$ to CF$_3$CH=CFCF$_2$CF$_3$ and CF$_3$CF=CHCF$_2$CF$_3$ Over Carbonaceous Catalyst Following the procedure of Example 3, a mixture of nitrogen (10 mL/min, 1.7×10$^{-7}$ m$^3$/s) and CF$_3$CHFCHFCF$_2$CF$_3$ (5 mL of liquid/hour) was passed through the reactor. GC analyses of the reactor effluent at several conditions are summarized in Table 11. In Table 11, temp is temperature, unks is unknowns, and other HFCs include CHF$_3$, CF$_3$CHF$_2$, and CF$_3$CH$_2$F.

TABLE 11

| Reactor temp, °C. | N₂ flow, sccm | Unks | Z-$CF_3CF=CHCF_2CF_3$ | Z-$CF_3CH=CFCF_2CF_3$ | Other $C_5HF_9s$ | $CF_3CHFCHFCF_2CF_3$ | Other $C_5H_2F_{10}s$ | Other HFCs |
|---|---|---|---|---|---|---|---|---|
| 200 | 20 | 1.47 | 12.9 | 29.6 | 0.36 | 55.0 | 0.65 | 0.08 |
| 200 | 20 | 2.05 | 10.7 | 24.3 | 0.29 | 62.1 | 0.47 | 0.09 |
| 250 | 20 | 2.24 | 28.1 | 59.6 | 1.30 | 1.01 | 7.43 | 0.09 |
| 250 | 20 | 2.07 | 28.1 | 59.9 | 1.30 | 1.00 | 7.35 | 0.33 |
| 250 | 40 | 2.14 | 28.9 | 60.2 | 1.35 | 0.90 | 6.25 | 0.32 |

Example 10

Phase Studies of Mixtures of HF and E-$CF_3CH=CHF$

A phase study was performed for a composition consisting essentially of E-$CF_3CH=CHF$ and HF, wherein the composition was varied and the vapor pressures were measured at both 20° C. and 70° C. Based upon the data from the phase studies, azeotropic compositions at other temperature and pressures have been calculated.

Table 12 provides a compilation of experimental and calculated azeotropic compositions for HF and E-$CF_3CH=CHF$ at specified temperatures and pressures.

TABLE 12

| Temperature, °C. | Pressure, psi (kPA) | Mole % HF | Mole % E-$CF_3CH=CHF$ |
|---|---|---|---|
| −20 | 15.5 (107) | 27.3 | 72.7 |
| 0 | 35.6 (242) | 29.7 | 70.3 |
| 20 | 70.4 (485) | 30.7 | 69.3 |
| 40 | 127 (878) | 31.5 | 68.5 |
| 60 | 215 (1482) | 31.6 | 68.4 |
| 65 | 242 (1669) | 31.5 | 68.5 |
| 70 | 273 (1881) | 31.4 | 68.6 |
| 75 | 307 (2117) | 31.2 | 68.8 |
| 80 | 345 (2376) | 31.0 | 69.0 |
| 85 | 386 (2661) | 30.7 | 69.3 |
| 90 | 431 (2972) | 30.4 | 69.6 |
| 95 | 482 (3323) | 30.0 | 70.0 |
| 100 | 539 (3715) | 29.5 | 70.5 |

Example 11

Phase Studies of Mixtures of HF and Z—$CF_3CF=CHF$

A phase study was performed for a composition consisting essentially of Z—$CF_3CF=CHF$ and HF, wherein the composition was varied and the vapor pressures were measured at both 19.5° C. and 70° C. Based upon the data from the phase studies, azeotrope compositions at other temperature and pressures have been calculated.

Table 13 provides a compilation of experimental and calculated azeotrope compositions for HF and Z—$CF_3CF=CHF$ at specified temperatures and pressures.

TABLE 13

| Temperature, °C. | Pressure, psi (kPa) | Mole % HF | Mole % Z-$CF_3CF=CHF$ |
|---|---|---|---|
| −25 | 12.8 (88.3) | 31.0 | 69.0 |
| −20 | 16.7 (115) | 31.7 | 68.3 |
| −10 | 24.7 (170) | 32.6 | 67.4 |

TABLE 13-continued

| Temperature, °C. | Pressure, psi (kPa) | Mole % HF | Mole % Z-$CF_3CF=CHF$ |
|---|---|---|---|
| 0 | 36.5 (252) | 33.4 | 66.6 |
| 19.5 | 72.1 (497) | 34.4 | 65.6 |
| 25 | 85.8 (592) | 34.5 | 65.5 |
| 50 | 175 (1208) | 35.0 | 65.0 |
| 75 | 323 (2226) | 35.2 | 64.8 |
| 77 | 335 (2308) | 35.2 | 64.8 |
| 80 | 361 (2490) | 35.3 | 64.7 |
| 85 | 403 (2777) | 35.3 | 64.7 |
| 90 | 448 (3090) | 35.4 | 64.6 |
| 95 | 497 (3429) | 35.4 | 64.6 |
| 100 | 551 (3799) | 35.5 | 64.5 |

Example 12

Phase Studies of Mixtures of HF and a Mixture of Z—$CF_3CH=CFCF_2CF_3$ and Z—$CF_3CF=CHCF_2CF_3$ A phase study was performed for a composition consisting essentially of a mixture of Z—$CF_3CH=CFCF_2CF_3$ and Z—$CF_3CF=CHCF_2CF_3$ and HF, wherein the composition was varied and the vapor pressures were measured at both 20° C. and 70° C. Based upon the data from the phase studies, azeotrope compositions at other temperature and pressures have been calculated.

Table 14 provides a compilation of experimental and calculated azeotrope compositions for HF and a mixture of Z—$CF_3CH=CFCF_2CF_3$ and Z—$CF_3CF=CHCF_2CF_3$ at specified temperatures and pressures.

TABLE 14

| Temperature, °C. | Pressure, psi (kPa) | Mole % HF | Mole % Z-$CF_3CH=CFCF_2CF_3$ and Z-$CF_3CF=CHCF_2CF_3$ |
|---|---|---|---|
| −20 | 4.1 (28.3) | 88.6 | 11.4 |
| −15 | 5.3 (36.5) | 87.8 | 12.2 |
| −10 | 6.7 (46.2) | 87.0 | 13.0 |
| −5 | 8.5 (58.6) | 86.2 | 13.8 |
| 0 | 10.6 (73.1) | 85.3 | 14.7 |
| 20 | 24.2 (167) | 82.0 | 18.0 |
| 40 | 49.3 (340) | 78.6 | 21.4 |
| 60 | 92.8 (639) | 75.1 | 24.9 |
| 65 | 108 (742) | 74.2 | 25.8 |
| 70 | 124 (855) | 73.4 | 26.6 |
| 75 | 143 (988) | 72.5 | 27.5 |
| 80 | 165 (1136) | 71.6 | 28.4 |
| 85 | 189 (1300) | 70.6 | 29.4 |
| 90 | 217 (1495) | 69.7 | 30.3 |
| 95 | 248 (1713) | 68.6 | 31.4 |
| 100 | 285 (1965) | 67.4 | 32.6 |

Example 13

Phase Studies of Mixtures of HF and $CF_3CHFCHFCF_2CF_3$

A phase study was performed for a composition consisting essentially of $CF_3CHFCHFCF_2CF_3$ and HF, wherein the composition was varied and the vapor pressures were measured at both 30° C. and 80° C. Based upon the data from the phase studies, azeotrope compositions at other temperature and pressures have been calculated.

Table 15 provides a compilation of experimental and calculated azeotrope compositions for HF and $CF_3CHFCHFCF_2CF_3$ at specified temperatures and pressures.

TABLE 15

| Temperature, ° C. | Pressure, psi (kPa) | Mole % HF | Mole % $CF_3CHFCHFCF_2CF_3$ |
|---|---|---|---|
| −20 | 3.0 (20.7) | 97.3 | 2.7 |
| 0 | 7.7 (53.1) | 95.5 | 4.5 |
| 20 | 17.3 (119) | 93.2 | 6.8 |
| 30 | 25.0 (172) | 91.9 | 8.1 |
| 39.5 | 34.7 (239) | 90.7 | 9.3 |
| 40 | 35.3 (243) | 90.6 | 9.4 |
| 60 | 66.6 (459) | 87.8 | 12.2 |
| 65 | 77.3 (533) | 87.0 | 13.0 |
| 70 | 89.3 (616) | 86.3 | 13.7 |
| 75 | 103 (710) | 85.5 | 14.5 |
| 80 | 118 (814) | 84.8 | 15.2 |
| 85 | 135 (931) | 84.0 | 16.0 |
| 90 | 154 (1062) | 83.3 | 16.7 |
| 95 | 175 (1207) | 82.6 | 72.4 |
| 97.2 | 185 (1276) | 82.2 | 17.8 |
| 100 | 198 (1365) | 81.8 | 18.2 |

Example 14

Phase Studies of Mixtures of HF and $CF_3CF=CH_2$

A phase study was performed for a composition consisting essentially of $CF_3CF=CH_2$ and HF, wherein the composition was varied and the vapor pressures were measured at both 9.3° C. and 44.4° C. Based upon the data from the phase studies, azeotrope compositions at other temperature and pressures have been calculated.

Table 16 provides a compilation of experimental and calculated azeotrope compositions for HF and $CF_3CF=CH_2$ at specified temperatures and pressures.

TABLE 16

| Temperature, ° C. | Pressure, psi (kPa) | Mole % HF | Mole % $CF_3CF=CH_2$ |
|---|---|---|---|
| −20 | 23.2 (160) | 19.3 | 80.7 |
| −18.5 | 24.7 (170) | 19.7 | 80.3 |
| 0 | 49.5 (341) | 23.0 | 77.0 |
| 9.3 | 67.6 (466) | 24.4 | 75.6 |
| 20 | 94.6 (652) | 25.7 | 74.3 |
| 40 | 167 (1151) | 27.7 | 72.3 |
| 44.4 | 187 (1289) | 28.0 | 72.0 |
| 60 | 278 (1917) | 29.5 | 70.5 |
| 70 | 354 (2441) | 30.3 | 69.7 |
| 71.2 | 365 (2517) | 30.4 | 69.6 |
| 75 | 400 (2758) | 30.7 | 69.3 |
| 80 | 453 (3123) | 31.1 | 68.9 |

Example 15

Phase Studies of Mixtures of HF and $CF_3CH=CF_2$

A phase study was performed for a composition consisting essentially of $CF_3CH=CF_2$ and HF, wherein the composition was varied and the vapor pressures were measured at both 0.3° C. and 50.1° C. Based upon the data from the phase studies, azeotrope compositions at other temperature and pressures have been calculated.

Table 17 provides a compilation of experimental and calculated azeotrope compositions for HF and $CF_3CH=CF_2$ at specified temperatures and pressures.

TABLE 17

| Temperature, ° C. | Pressure, psi (kPa) | Mole % HF | Mole % $CF_3CH=CF_2$ |
|---|---|---|---|
| −20 | 17.4 (120) | 29.6 | 70.4 |
| −17 | 19.7 (136) | 29.9 | 70.1 |
| −3 | 34.7 (239) | 31.0 | 69.0 |
| 0 | 38.8 (267) | 30.9 | 69.1 |
| 0.3 | 39.2 (270) | 30.9 | 69.1 |
| 3.9 | 44.7 (308) | 31.0 | 69.0 |
| 20 | 76.7 (529) | 32.8 | 67.2 |
| 40 | 139 (958) | 34.0 | 66.0 |
| 50.1 | 183 (1262) | 34.5 | 65.5 |
| 60 | 236 (1627) | 34.9 | 65.1 |
| 65 | 268 (1848) | 35.1 | 64.9 |
| 70 | 304 (2096) | 35.3 | 64.7 |
| 71.5 | 314.7 (2170) | 35.4 | 64.6 |
| 75 | 344 (2372) | 35.6 | 64.4 |
| 80 | 389 (2682) | 35.3 | 64.7 |
| 85 | 441 (3041) | 36.0 | 64.0 |
| 90 | 524 (3613) | 36.9 | 63.1 |
| 95 | 629 (4337) | 37.4 | 62.6 |
| 100 | 745 (5137) | 38.0 | 62.0 |

Example 16

Phase Studies of Mixtures of HF and a Mixture of $Z—C_2F_5CF=CHCF_2C_2F_5$ and $Z—C_2F_5CH=CFCF_2C_2F_5$ A phase study was performed for a composition consisting essentially of HF and a mixture of $Z—C_2F_5CF=CHCF_2C_2F_5$ and $Z—C_2F_5CH=CFCF_2C_2F_5$, wherein the composition was varied and the vapor pressure were measured at both 19.9° C. and 69.6° C. Based upon the data from the phase studies, azeotrope compositions at other temperature and pressures have been calculated.

Table 18 provides a compilation of experimental and calculated azeotrope compositions for HF and a mixture of $Z—C_2F_5CF=CHCF_2C_2F_5$ and $Z—C_2F_5CH=CFCF_2C_2F_5$ at specified temperatures and pressures.

TABLE 18

| Temperature, ° C. | Pressure, psi (kPa) | Mole % HF | Mole % $Z\text{-}C_2F_5CF=CHCF_2C_2F_5$ and $Z\text{-}C_2F_5CH=CFCF_2C_2F_5$ |
|---|---|---|---|
| −20 | 2.9 (20.0) | 98.7 | 1.3 |
| −15 | 3.7 (25.5) | 98.5 | 1.5 |
| −10 | 4.7 (32.4) | 98.3 | 1.7 |
| −5 | 5.9 (40.7) | 98.1 | 1.9 |
| 0 | 7.3 (50.3) | 97.9 | 2.1 |
| 19.9 | 16.3 (112) | 96.7 | 3.3 |
| 20 | 16.3 (112) | 96.7 | 3.3 |
| 25.1 | 19.7 (136) | 96.4 | 3.6 |

TABLE 18-continued

| Temperature, °C. | Pressure, psi (kPa) | Mole % HF | Mole % Z-$C_2F_5CF=CHCF_2C_2F_5$ and Z-$C_2F_5CH=CFCF_2C_2F_5$ |
|---|---|---|---|
| 40 | 33.2 (229) | 95.4 | 4.6 |
| 60 | 62.3 (430) | 93.9 | 6.1 |
| 65 | 72.1 (497) | 93.5 | 6.5 |
| 69.6 | 82.2 (567) | 93.1 | 6.9 |
| 70 | 83.3 (574) | 93.1 | 6.9 |
| 75 | 95.7 (660) | 92.7 | 7.3 |
| 80 | 110 (758) | 92.3 | 7.7 |
| 85 | 125 (862) | 91.9 | 8.1 |
| 90 | 143 (986) | 91.5 | 8.5 |
| 95 | 162 (1117) | 91.2 | 8.8 |
| 100 | 183 (1262) | 90.8 | 9.2 |
| 108.4 | 225 (1551) | 90.3 | 9.7 |

Example 17

Phase Studies of Mixtures of HF and $C_2F_5CHFCHFCF_2C_2F_5$

A phase study was performed for a composition consisting essentially of $C_2F_5CHFCHFCF_2C_2F_5$ and HF, wherein the composition was varied and the vapor pressures were measured at both 30.8° C. and 80.2° C. Based upon the data from the phase studies, azeotrope compositions at other temperature and pressures have been calculated.

Table 19 provides a compilation of experimental and calculated azeotrope compositions for HF and $C_2F_5CHFCHFCF_2C_2F_5$ at specified temperatures and pressures.

TABLE 19

| Temperature, °C. | Pressure, psi (kPa) | Mole % HF | Mole % $C_2F_5CHFCHFCF_2C_2F_5$ |
|---|---|---|---|
| 13.5 | 11.9 (82.0) | <100 | 0.003 |
| 14 | 12.1 (83.4) | 99.9 | 0.1 |
| 14.5 | 12.3 (84.8) | 99.9 | 0.1 |
| 15 | 12.6 (86.9) | 99.8 | 0.2 |
| 20 | 15.1 (104) | 99.3 | 0.7 |
| 25 | 18.1 (125) | 98.8 | 1.2 |
| 27.4 | 19.7 (136) | 98.6 | 1.4 |
| 30 | 21.6 (149) | 98.5 | 1.5 |
| 30.8 | 22.2 (153) | 98.5 | 1.5 |
| 40 | 30.3 (209) | 98.2 | 1.8 |
| 50 | 41.7 (288) | 97.7 | 2.3 |
| 60 | 56.5 (390) | 97.3 | 2.7 |
| 70 | 75.3 (519) | 96.8 | 3.2 |
| 80 | 99.1 (683) | 96.3 | 3.7 |
| 80.2 | 99.6 (687) | 96.3 | 3.7 |
| 90 | 129 (889) | 95.8 | 4.2 |
| 99.8 | 165 (1138) | 95.4 | 4.6 |
| 100 | 165 (1138) | 95.4 | 4.6 |
| 110 | 210 (1484) | 95.0 | 5.0 |
| 120 | 264 (1820) | 94.7 | 5.3 |

Example 18

Azeotropic Distillation for Separation of E-$CF_3CH=CHF$ from $CF_3CH_2CHF_2$

A mixture of HF, E-$CF_3CH=CHF$, and $CF_3CH_2CHF_2$ is fed to a distillation column for the purpose of purification of the E-$CF_3CH=CHF$. The data in Table 20 were obtained by calculation using measured and calculated thermodynamic properties.

TABLE 20

| Component or variable | Column feed | Column overhead (distillate) | Column bottoms |
|---|---|---|---|
| $CF_3CH_2CHF_2$, mol % | 17.6 | 0.7 ppm | 100 |
| E-$CF_3CH=CHF$, mol % | 76.5 | 92.9 | 3 ppm |
| HF, mol % | 5.9 | 7.1 | — |
| Temp, °C. | — | −6.8 | 31.1 |
| Pressure, psi (kPa) | — | 24.7 (170) | 26.7 (184) |

Example 19

Azeotropic Distillation for Separation of Z—$CF_3CF=CHF$ from $CF_3CHFCHF_2$

A mixture of HF, Z—$CF_3CF=CHF$, and $CF_3CHFCHF_2$ is fed to a distillation column for the purpose of purification of the Z—$CF_3CF=CHF$. The data in Table 21 were obtained by calculation using measured and calculated thermodynamic properties.

TABLE 21

| Component or variable | Column feed | Column overhead (distillate) | Column bottoms |
|---|---|---|---|
| $CF_3CHFCHF_2$, mol % | 24.4 | 1 ppm | 99.99 |
| Z-$CF_3CF=CHF$, mol % | 51.2 | 67.7 | 68 ppm |
| HF, mol % | 24.4 | 32.3 | trace |
| Temp, °C. | — | −8.3 | 21.8 |
| Pressure, psi (kPa) | — | 24.7 (170) | 26.7 (184) |

Example 20

Azeotropic Distillation for Separation of Z—$CF_3CH=CFCF_2CF_3$ and Z—$CF_3CF=CHCF_2CF_3$ from $CF_3CHFCHFCF_2CF_3$ A mixture of HF, Z—$CF_3CH=CFCF_2CF_3$ and Z—$CF_3CF=CHCF_2CF_3$, and $CF_3CHFCHFCF_2CF_3$ is fed to a distillation column for the purpose of purification of Z—$CF_3CH=CFCF_2CF_3$ and Z—$CF_3CF=CHCF_2CF_3$. The data in Table 22 were obtained by calculation using measured and calculated thermodynamic properties.

TABLE 22

| Component or variable | Column feed | Column overhead (distillate) | Column bottoms |
|---|---|---|---|
| $CF_3CHFCHFCF_2CF_3$, mol % | 33.4 | 1 ppm | 100 |
| Z-$CF_3CH=CFCF_2CF_3$ and Z-$CF_3CF=CHCF_2CF_3$, mol % | 33.3 | 50.0 | 2 ppm |
| HF, mol % | 33.3 | 50.0 | — |
| Temp, °C. | — | 30.0 | 21.8 |
| Pressure, psi (kPa) | — | 19.7 (136) | 21.7 (150) |

Example 21

Azeotropic Distillation for Separation of $CF_3CF=CH_2$ from $CF_3CF_2CH_3$

A mixture of HF, $CF_3CF=CH_2$, and $CF_3CF_2CH_3$ is fed to a distillation column for the purpose of purification of $CF_3CF=CH_2$. The data in Table 23 were obtained by calculation using measured and calculated thermodynamic properties.

TABLE 23

| Component or variable | Column feed | Column overhead (distillate) | Column bottoms |
|---|---|---|---|
| $CF_3CF_2CH_3$, mol % | 27.3 | 10 ppm | 100 |
| $CF_3CF=CH_2$, mol % | 63.6 | 87.5 | 27 ppm |
| HF, mol % | 9.1 | 12.5 | — |
| Temp, ° C. | — | −17.2 | −2.7 |
| Pressure, psi (kPa) | — | 24.7 (170) | 26.7 (184) |

Example 22

Azeotropic Distillation for Separation of $CF_3CH=CF_2$ from $CF_3CH_2CF_3$

A mixture of HF, $CF_3CH=CF_2$, and $CF_3CH_2CF_3$ is fed to a distillation column for the purpose of purification of the $CF_3CH=CF_2$. The data in Table 24 were obtained by calculation using measured and calculated thermodynamic properties.

TABLE 24

| Component or variable | Column feed | Column overhead (distillate) | Column bottoms |
|---|---|---|---|
| $CF_3CH_2CF_3$, mol % | 17.6 | 10 ppm | 99.99 |
| $CF_3CH=CF_2$, mol % | 76.5 | 92.9 | 78 ppm |
| HF, mol % | 5.9 | 7.1 | — |
| Temp, ° C. | — | −15.4 | 8.3 |

TABLE 24-continued

| Component or variable | Column feed | Column overhead (distillate) | Column bottoms |
|---|---|---|---|
| Pressure, psi (kPa) | — | 19.7 (136) | 21.7 (150) |

Example 23

Azeotropic Distillation for Separation of $Z-C_2F_5CF=CHCF_2C_2F_5$ and $Z-C_2F_5CH=CFCF_2C_2F_5$ from $C_2F_5CHFCHFCF_2C_2F_5$ A mixture of HF, $Z-C_2F_5CF=CHCF_2C_2F_5$ and $Z-C_2F_5CH=CFCF_2C_2F_5$, and $C_2F_5CHFCHFCF_2C_2F_5$ is fed to a distillation column for the purpose of purification of $Z-C_2F_5CF=CHCF_2C_2F_5$ and $Z-C_2F_5CH=CFCF_2C_2F_5$. The data in Table 25 were obtained by calculation using measured and calculated thermodynamic properties.

TABLE 25

| Component or variable | Column feed | Column overhead (distillate) | Column bottoms |
|---|---|---|---|
| $C_2F_5CHFCHFCF_2C_2F_5$, mol % | 33.4 | 1 ppm | 100 |
| $Z-C_2F_5CF=CHCF_2C_2F_5$ and $Z-C_2F_5CH=CFCF_2C_2F_5$, mol % | 33.3 | 50.0 | 8 ppm |
| HF, mol % | 33.3 | 50.0 | — |
| Temp, ° C. | — | 75.4 | 107 |
| Pressure, psi (kPa) | — | 19.7 (136) | 21.7 (150) |

Example 24

Two-column Azeotropic Distillation for Separation of $E-CF_3CH=CHF$ from HF

A mixture of HF and $E-CF_3CH=CHF$ is fed to a distillation set-up comprising 2 columns in series, the first at high pressure (HP) and the second at low pressure (LP). The data in Table 26 were obtained by calculation using measured and calculated thermodynamic properties. The numbers at the top of the columns refer to FIG. 1.

TABLE 26

| Compound or variable | 540 Feed Mixture | 570 Column (510) distillate | 566 $E-CF_3CH=CHF$ product | 585 Column (520) distillate | 586 HF product |
|---|---|---|---|---|---|
| $E-CF_3CH=CHF$, mol % | 76.0 | 69.0 | 100 | 72.0 | — |
| HF, mol % | 24.0 | 31.0 | — | 28.0 | 100 |
| Temp, ° C. | — | 68.6 | 76.1 | −18.3 | 26.2 |
| Pres, psi (kPa) | — | 265 (1827) | 267 (1841) | 16.7 (115) | 18.7 (129) |

Example 25

Two-column Azeotropic Distillation for Separation of Z—$CF_3CF$=CHF from HF

A mixture of HF and Z—HFC-1225ye is fed to a distillation process for the purpose of purification of the Z—HFC-1225ye. The data in Table 27 were obtained by calculation using measured and calculated thermodynamic properties. The numbers at the top of the columns refer to FIG. 1.

TABLE 27

| Compound or variable | 540 Feed Mixture | 570 Column (510) distillate | 566 Z-$CF_3CF$=CHF product | 585 Column (520) distillate | 586 HF product |
|---|---|---|---|---|---|
| HF, mol % | 26.7 | 35.0 | trace | 32.0 | 100 |
| Z-$CF_3CF$=CHF, mol % | 73.3 | 65.0 | 100 | 68.0 | — |
| Temp., ° C. | — | 76.6 | 86.0 | −19.2 | 26.2 |
| Pres., psi (kPa) | — | 334.7 (2307) | 336.7 (2321) | 16.7 (115) | 18.7 (129) |

Example 26

Two-Column Azeotropic Distillation for Separation of Z—$CF_3CH$=$CFCF_2CF_3$ and Z—$CF_3CF$=$CHCF_2CF_3$ from HF A mixture of HF and Z—$CF_3CH$=$CFCF_2CF_3$ and Z—$CF_3CF$=$CHCF_2CF_3$ is fed to a distillation process for the purpose of purification of the Z—$CF_3CH$=$CFCF_2CF_3$ and Z—$CF_3CF$=$CHCF_2CF_3$. The data in Table 28 were obtained by calculation using measured and calculated thermodynamic properties. The numbers at the top of the columns refer to FIG. 1.

TABLE 28

| Compound or variable | 540 Feed Mixture | 570 Column (510) distillate | 566 HF product | 585 Column (520) distillate | 586 Z-$CF_3CH$=$CFCF_2CF_3$ and Z-$CF_3CF$=$CHCF_2CF_3$ product |
|---|---|---|---|---|---|
| HF, mol % | 73.9 | 70.0 | 100 | 82.5 | 100 |
| Z-$CF_3CH$=$CFCF_2CF_3$ and Z-$CF_3CF$=$CHCF_2CF_3$, mol % | 26.1 | 30.0 | — | 17.5 | — |
| Temp., ° C. | — | 91.7 | 117.5 | 14.9 | 39.8 |
| Pres., psi (kPa) | — | 224.7 (1549) | 226.7 (1563) | 19.7 (136) | 21.7 (150) |

Example 27

Two-column Azeotropic Distillation for Separation of $CF_3CF$=$CH_2$ from HF A mixture of HF and $CF_3CF$=$CH_2$ is fed to a distillation process for the purpose of purification of the $CF_3CF$=$CH_2$. The data in Table 29 were obtained by calculation using measured and calculated thermodynamic properties. The numbers at the top of the columns refer to FIG. 1.

TABLE 29

| Compound or variable | 540 Feed Mixture | 570 Column (510) distillate | 566 $CF_3CF=CH_2$ product | 585 Column (520) distillate | 586 HF product |
|---|---|---|---|---|---|
| HF, mol % | 16.0 | 30.0 | — | 20.0 | 100 |
| $CF_3CF=CH_2$, mol % | 84.0 | 70.0 | 100 | 80.0 | — |
| Temp., °C. | — | 71.2 | 80.2 | −18.4 | 36.9 |
| Pres., psi (kPa) | — | 364.7(2515) | 366.7 (2528) | 24.7 (170) | 26.7 (184) |

Example 28

Two-column Azeotropic Distillation for Separation of $CF_3CH=CF_2$ from HF

A mixture of HF and $CF_3CH=CF_2$ is fed to a distillation process for the purpose of purification of the $CF_3CH=CF_2$. The data in Table 30 were obtained by calculation using measured and calculated thermodynamic properties. The numbers at the top of the columns refer to FIG. 1.

TABLE 30

| Compound or variable | 540 Feed Mixture | 570 Column (510) distillate | 566 $CF_3CH=CF_2$ product | 585 Column (520) distillate | 586 HF product |
|---|---|---|---|---|---|
| HF, mol % | 30.4 | 24.1 | — | 30.5 | 100 |
| $CF_3CH=CF_2$, mol % | 69.6 | 75.9 | 100 | 69.5 | — |
| Temp., °C. | — | 71.5 | 80.1 | −17.1 | 30.6 |
| Pres., psi (kPa) | — | 314.7 (2170) | 316.7 (2184) | 19.7 (136) | 21.7 (150) |

Example 29

Two-column Azeotropic Distillation for Separation of Z—$C_2F_5CF=CHCF_2C_2F_5$ and Z—$C_2F_5CH=CFCF_2C_2F_5$ from HF A mixture of HF and Z—$C_2F_5CF=CHCF_2C_2F_5$ and Z—$C_2F_5CH=CFCF_2C_2F_5$ is fed to a distillation process for the purpose of purification of the Z—$C_2F_5CF=CHCF_2C_2F_5$ and Z—$C_2F_5CH=CFCF_2C_2F_5$. The data in Table 31 were obtained by calculation using measured and calculated thermodynamic properties. The numbers at the top of the columns refer to FIG. 1.

TABLE 31

| Compound or variable | 540 Feed Mixture | 570 Column (510) distillate | 566 Z-$C_2F_5CF=CHCF_2C_2F_5$ and Z-$C_2F_5CH=CFCF_2C_2F_5$ product | 585 Column (520) distillate | 586 HF product |
|---|---|---|---|---|---|
| HF, mol % | 93.9 | 95.8 | 100 | 91.0 | 100 |
| Z-$C_2F_5CF=CHCF_2C_2F_5$ and Z-$C_2F_5CH=CFCF_2C_2F_5$, mol % | 6.1 | 4.2 | — | 9.0 | — |
| Temp., °C. | — | 26.9 | 84.8 | 109 | 117.5 |
| Pres., psi (kPa) | — | 19.7 (136) | 21.7 (150) | 224.7 (1549) | 226.7 (1563) |

Examples 30-33

Examples 30-33 use one of three reactors:

Reactor A: Inconel® 600 tube (this alloy is about 76 wt % nickel), 18 in (45.7 cm) long×1.0 in (2.5 cm) outer diameter×0.84 in (2.1 cm) inner diameter. Tube wall thickness is 0.16 in (0.41 cm). The preheat zone is 7 in (17.8 cm) long. The reaction zone is 2 in (5.1 cm) long. The quench zone is 7 in (17.8 cm) long. The tube is heated with 1 in (2.5 cm) diameter ceramic band heaters. The leads of a 7-point thermocouple are distributed long the length of the tube, with some in the middle of the reactor zone (to measure gas temperature).

Reactor B: Schedule 80 Nickel 200 tube with an Inconel® 617 overlay, 18 in (45.7 cm) long, 1.5 in (3.8 cm) outer diameter, 0.84 in (2.1 cm) inner diameter. The reaction zone is 2 in (5.1 cm) long. The reactor zone is heated with an 8.5 in (21.6 cm) long×2.5 in (6.35 cm) split tube furnace. The leads of a 7-point thermocouple are distributed long the length of the tube, with some in the middle of the reactor zone (to measure gas temperature).

Reactor C: Hastelloy® C276 with gold lining. Length 5 in (12.7 cm)×0.50 in (1.3 cm) outer diameter×0.35 in (0.89 cm) inner diameter. The wall thickness is 0.15 in (3.8 mm). The thickness of the gold lining is 0.03 in (0.08 cm). The reactor zone is 2 in (5.1 cm) long and is heated with a ceramic band heater.

Example 30

Reactor A (Inconel® 600 reaction surface) is used. The reactor inlet gas temperature ("Reactor Inlet T Gas" in Table 1) is the reaction temperature. Two runs are made at reaction temperatures of 724° C. and 725° C., respectively. In Run A, the reactant feed is undiluted with inert gas. In Run B, helium and reactant are fed in the ratio of 1.4:1. The benefit of the inert gas diluent is seen in the improved yield of Run B (80%)

over that of Run A (71%). A lower concentration of fluorocarbon byproducts are made in Run B. Results are summarized in Table 32. Note that "sccm" in the table stands for "standard cubic centimeters per minute".

TABLE 32

|  | A | B |
|---|---|---|
| Reactor Conditions, Feeds | | |
| Preheat Control T setting | 700° C. | 700° C. |
| Preheat Gas T 1" | 545° C. | 572° C. |
| Preheat Gas T 2" | 635° C. | 655° C. |
| Preheat Gas T 3" | 690° C. | 696° C. |
| Preheat Gas T 4" | 718° C. | 720° C. |
| Reactor Control T setting | 700° C. | 700° C. |
| Reactor Inlet T wall | 711° C. | 710° C. |
| Reactor Middle T wall | 700° C. | 700° C. |
| Reactor Exit T wall | 622° C. | 623° C. |
| Reactor Inlet T gas | 724° C. | 725° C. |
| Reactor Middle T gas | 714° C. | 716° C. |
| Reactor Exit T gas | 675° C. | 673° C. |
| HFC-236fa Feed sccm | 25 sccm | 25 sccm |
| Helium Feed sccm | 0 sccm | 35 sccm |
| Residence Time in Reaction Zone (seconds) | 42 | 18 |
| Gas Chromatograph Results in Mole % | | |
| $CHCF_3$ (HFC-23) | 4.5 | 2.1 |
| $CF_3CH{=}CF_2$ (HFC-1225zc) | 51.6 | 47.7 |
| Octafluorocyclobutane (PFC-C318) | 1.8 | 2.0 |
| $CF_3CH_2CF_3$ (HFC-236fa) | 27.5 | 40.3 |
| $C_4H_2F_6$ (HFC-1336) | 1.8 | 0.7 |
| $C_4HF_7$ (HFC-1327) | 1.7 | 1.2 |
| $C_4HF_9$ (HFC-329) | 4.2 | 2.1 |
| Other | 3.1 | 2.1 |
| Unknown | 3.8 | 1.8 |
| Conversion (%) | 72.5 | 59.7 |
| Yield (%) | 71 | 80 |

Example 31

Reactor A (Inconel® 600 reaction surface) is used in this study of the effect of temperature on conversion and yield. Run A is made at reactor temperature of 600° C. Runs B and C are made at 699° C. and 692° C., respectively. Runs A and B are diluted 4:1 with helium. Run C is undiluted. Run A (600° C.) conversion is low at 0.3%. Runs B and C (690-700° C.) have higher conversion, though still low compared to the conversion seen in Example 30, which was run at 725° C. and appreciably longer reaction zone residence times. Yields are reported, however are not reliable for such low conversions. The dependence of conversion on temperature and reaction zone residence time is plain from these experiments. Results are summarized in Table 33.

TABLE 33

|  | A | B | C |
|---|---|---|---|
| Reactor Conditions, Feeds | | | |
| Preheat Control T setting (° C.) | 600 | 700 | 700 |
| Preheat Gas T 1" (° C.) | 417 | 497 | 443 |
| Preheat Gas T 2" (° C.) | 511 | 604 | 546 |
| Preheat Gas T 3" (° C.) | 563 | 660 | 623 |
| Preheat Gas T 4" (° C.) | 592 | 691 | 676 |
| Reactor Control T setting (° C.) | 601 | 700 | 700 |
| Reactor Inlet T wall (° C.) | 615 | 718 | 722 |
| Reactor Middle T wall (° C.) | 601 | 700 | 700 |
| Reactor Exit T wall (° C.) | 566 | 661 | 653 |
| Reactor Inlet T gas (° C.) | 600 | 699 | 692 |
| Reactor Middle T gas (° C.) | 588 | 684 | 665 |

TABLE 33-continued

|  | A | B | C |
|---|---|---|---|
| Reactor Exit T gas (° C.) | 560 | 650 | 609 |
| Helium Feed sccm | 400 | 400 | 0 |
| HFC-236fa Feed sccm | 100 | 100 | 200 |
| Residence Time in Reaction Zone (seconds) | 2 | 2 | 5 |
| Gas Chromatograph Results in Mole % | | | |
| $CHCF_3$ (HFC-23) | 0.0 | 0.0 | 0.1 |
| $CHF{=}CF_2$ (HFC-1123) | 0.0 | 0.0 | 0.1 |
| $CF_3CH{=}CF_2$ (HFC-1225zc) | 0.1 | 2.1 | 4.4 |
| $CF_3CH_2CF_3$ (HFC-236fa) | 99.7 | 97.6 | 95.3 |
| Other (<1%) | 0.2 | 0.2 | 0.3 |
| Conversion (%) | 0.3 | 2.4 | 4.7 |
| Yield (%) | 33 | 87.5 | 93.6 |

Example 32

Reactor B (Nickel 200 reaction surface) is used. In this reactor the reactor temperature is the reactor center gas temperature ("Reactor Center Gas T" in Table 3). Runs A, B, and C are made at 800° C. with helium:reactant ratios of 0:1, 1:1, and 2:1, respectively. At these temperatures, higher than in Example 30, and at comparable reaction zone residence times, on the nickel surface, conversions are as high, and yields higher. In pyrolyses, higher temperatures generally lead to lower yields because of increased rates of undesirable side reactions giving unwanted byproducts. That this is not seen in Example 32 is testimony to the superiority of the nickel reaction surface to the nickel alloy reaction surface of Example 30. Further support for this conclusion is found in Run D, made at 850° C. with 4:1 helium dilution. Conversion is high at 76.9%, and the yield is 90.5%, the best of any of the Example 32 runs. Results are summarized in Table 34.

TABLE 34

|  | A | B | C | D |
|---|---|---|---|---|
| Reactor Conditions, Feeds | | | | |
| Reactor Control T setting (° C.) | 839 | 834 | 832 | 885 |
| Reactor Inlet T wall (° C.) | 812 | 806 | 804 | 853 |
| Reactor Middle T wall (° C.) | 831 | 826 | 824 | 877 |
| Reactor Exit T wall (° C.) | 808 | 805 | 804 | 855 |
| Preheat Gas T 1" (° C.) | 658 | 666 | 669 | 707 |
| Reactor Inlet gas T 2" (° C.) | 736 | 740 | 741 | 786 |
| Reactor Inlet gas T 3" (° C.) | 779 | 780 | 781 | 829 |
| Reactor Center gas T 4" (° C.) | 800 | 800 | 800 | 850 |
| Reactor Exit gas T 5" (° C.) | 800 | 800 | 799 | 851 |
| Reactor Exit gas T 6" (° C.) | 776 | 777 | 777 | 829 |
| Exit gas T 7" (° C.) | 738 | 741 | 740 | 791 |
| HFC-236fa Feed sccm | 200 | 200 | 200 | 200 |
| He Feed sccm | 0 | 200 | 400 | 800 |
| Residence Time in Reaction Zone (seconds) | 5 | 3 | 2 | 1 |
| GC Results in Mole % | | | | |
| $CHCF_3$ (HFC-23) | 4.1 | 2.5 | 2.0 | 2.5 |
| $CHF{=}CF_2$ (HFC-1123) | 0.7 | 1.0 | 1.0 | 1.4 |
| $CF_3CH{=}CF_2$ (HFC-1225zc) | 60.8 | 50.6 | 45.3 | 69.6 |
| $CF_3CH_2CF_3$ (HFC-236fa) | 28.2 | 37.7 | 50.2 | 23.1 |
| $C_4H_2F_6$ (HFC-1336) | 1.3 | 0.6 | 0.4 | 0.0 |
| Other (<1% produced) | 2.1 | 1.0 | 1.1 | 2.1 |
| Unknown | 2.8 | 6.6 | 0.0 | 1.2 |
| Conversion (%) | 71.8 | 62.3 | 49.8 | 76.9 |
| Yield (%) | 84.7 | 81.2 | 90.9 | 90.5 |

Example 33

Reactor C (gold reaction surface). Like nickel, the gold surface gives high yields and therefore reduced side reactions producing unwanted byproducts. The inert gas diluent effect (reduction) on conversion is less on gold than on nickel or nickel alloy surfaces. At 800° C. (Runs A and B) conversions are lower than those of Runs B and C of Example 32 but the average yield is higher. Results are summarized in Table 35.

TABLE 35

| Reactor Conditions, Feeds | | | | | | |
|---|---|---|---|---|---|---|
| | A | B | C | D | E | F |
| Reactor Temp (° C.) | 800 | 800 | 700 | 700 | 600 | 600 |
| He Feed sccm | 15 | 20 | 15 | 20 | 15 | 20 |
| HFC-236fa Feed sccm | 10 | 5 | 10 | 5 | 10 | 5 |
| Residence Time in Reaction Zone (seconds) | 8 | 8 | 8 | 8 | 8 | 8 |
| GC Mole % | | | | | | |
| $CHF_3$ and $CH_2F_2$ | 1.9 | 1.9 | 0.1 | 0.1 | ND* | ND |
| $CHF=CF_2$ (HFC-1123) | 0.8 | 0.9 | ND | ND | ND | ND |
| $CF_3CH_3$ (HFC-143a) | 0.2 | 0.2 | ND | ND | ND | ND |
| $CF_3CH=CF_2$ (HFC-1225zc) | 33.3 | 36.6 | 1.7 | 1.8 | 0.2 | 0.1 |
| $CF_3CHFCF_3$ (HFC-227ea) | 0.2 | 0.2 | 0.1 | 0.1 | 0.1 | 0.1 |
| $CF_3CH_2CF_3$ (HFC-236fa) | 61.9 | 58.4 | 97.6 | 97.6 | 99.4 | 99.5 |
| Unknown | 0.6 | 0.5 | 0.3 | 0.1 | 0.2 | 0.1 |
| Conversion (%) | 38.1 | 41.6 | 2.4 | 2.4 | 0.6 | 0.5 |
| Yield (%) | 87.4 | 88.0 | 71 | 75 | 33 | 20 |

*ND = not detected

* ND=not detected

Examples 30-33 show the specificity of the pyrolysis according to this invention, which gives the product $CF_3CH=CF_2$ in good yield at good conversion with only small amounts of unwanted byproducts. Nickel is superior to nickel alloy as the reaction surface in giving higher yields of product. Gold is superior to nickel.

Conversions are low up to about 700° C., being good at 725° C. and above with no deterioration in performance even at 850° C.

What is claimed is:

1. A process to produce an azeotrope composition comprising a hydrofluoroolefin containing 3 to 8 carbon atoms and hydrogen fluoride, said process comprising, dehydrofluorinating a hydrofluorocarbon containing at least one hydrogen and at least one fluorine on adjacent carbons, wherein said dehydrofluorinating is carried out in a reaction zone at a temperature from about 0° C. to about 1000° C., thereby forming a mixture comprising said hydrofluoroolefin, unreacted hydrofluorocarbon and hydrogen fluoride, wherein at least one of said hydrofluoroolefin and said hydrofluorocarbon are present in said product mixture as an azeotrope composition with hydrogen fluoride and are selected from the group consisting of
CH3CF2CHF2 and CHF2CF=CH2;
CF3CHFCH3 and CF3CH=CH2;
CF3CH2CH2F and CF3CH=CH2;
CHF2CH2CHF2 and CHF2CH=CHF;
CF3CH2CF2CF3 and CF3CH=CFCF3;
CF3CHFCHFCF3 and CF3CH=CFCF3;
CH3CF2CF2CF3 and CH2=CFCF2CF3;
CHF2CH2CF2CF3 and CHF2CH=CFCF3;
CH3CF2CF2CHF2 and CH2=CFCF2CHF2;
CHF2CH2CHFCF3 and CHF2CH=CHCF3;
CHF2CHFCH2CF3 and CHF2CH=CHCF3;
CF3CH2CHFCF2CF3 and CF3CH=CHCF2CF3;
CF3CHFCH2CF2CF3 and CF3CH=CHCF2CF3;
CF3CH2CHFCF2CF2CF3 and CF3CH=CHCF2CF2CF3;
CF3CHFCH2CF2CF2CF3 and CF3CH=CHCF2CF2CF3;
CH2FCHFCH2CF3 and CH2FCH=CHCF3;
CH3CF(CF3)2 and CH2=C(CF3)2;
(CF3)2CFCH2CF3 and (CF3)2C=CHCF3;
CH3CH2CF2CF2CF3 and CH3CH=CFCF2CF3;
C2F5CHFCH2CF2C2F5 and C2F5CH=CHCF2C2F5;
C2F5CH2CHFCF2C2F5 and C2F5CH=CHCF2C2F5;
CF3CHFCH2CF2CF2C2F5 and CFSCH=CHCF2CF2C2F5; and
CF3CH2CHFCF2CF2C2F5 and CF3CH=CHCF2CF2C2F5,
and distilling the mixture to produce a distillate composition comprising an azeotrope composition containing said hydrofluoroolefin and hydrogen fluoride and a column bottoms composition comprising said hydrofluorocarbon essentially free of hydrogen fluoride.

2. The process of claim 1 wherein the dehydrofluorinating is carried out in a reaction zone in the presence of catalyst.

3. The process of claim 2 wherein said catalyst comprises at least one catalyst selected from the group consisting of aluminum fluoride, fluorided alumina, metals on aluminum fluoride, metals on fluorided alumina; oxides, fluorides, and oxyfluorides of magnesium, zinc and mixtures of magnesium and zinc and/or aluminum; lanthanum oxide and fluorided lanthanum oxide; chromium oxides, fluorided chromium oxides, and cubic chromium trifluoride; and activated carbon, three dimensional matrix carbonaceous materials, and acid-washed carbon.

4. The process of claim 1, wherein said dehydrofluorinating is carried out in a reaction zone at a temperature from about 350° C. to about 1000° C. in the absence of catalyst.

* * * * *